US010583157B2

(12) United States Patent
Son et al.

(10) Patent No.: US 10,583,157 B2
(45) Date of Patent: Mar. 10, 2020

(54) ARTIFICIAL CARTILAGE CONTAINING CHONDROCYTES OBTAINED FROM COSTAL CARTILAGE AND PREPARATION PROCESS THEREOF

(71) Applicants: BIO SOLUTION CO., LTD., Seoul (KR); KOREA INSTITUTE OF RADIOLOGICAL & MEDICAL SCIENCES, Seoul (KR); UNIVERSITY-INDUSTRY COOPERATION GROUP OF KYUNGHEE UNIVERSITY, Yongin-si (KR)

(72) Inventors: Young Sook Son, Seoul (KR); Jung Sun Lee, Seoul (KR); Eun Kyung Lee, Seoul (KR); Jin Yeon Lee, Seoul (KR)

(73) Assignees: BIO SOLUTION CO., LTD., Seoul (KR); KOREA INSTITUTE OF RADIOLOGICAL & MEDICAL SCIENCES, Seoul (KR); UNIVERSITY-INDUSTRY COOPERATION GROUP OF KYUNGHEE UNIVERSITY, Yongin-si (KR)

( * ) Notice: Subject to any disclaimer, the term of this patent is extended or adjusted under 35 U.S.C. 154(b) by 49 days.

(21) Appl. No.: 15/620,093

(22) Filed: Jun. 12, 2017

(65) Prior Publication Data
US 2017/0274018 A1 Sep. 28, 2017

Related U.S. Application Data

(62) Division of application No. 12/159,204, filed as application No. PCT/KR2006/004479 on Jan. 31, 2006, now Pat. No. 9,694,034.

(30) Foreign Application Priority Data

Oct. 31, 2005 (KR) ........................ 10-2005-0103156

(51) Int. Cl.
| | |
|---|---|
| *A61K 35/28* | (2015.01) |
| *A61L 27/20* | (2006.01) |
| *A61L 27/38* | (2006.01) |
| *A61K 35/32* | (2015.01) |
| *C12N 5/077* | (2010.01) |
| *C12N 5/0775* | (2010.01) |
| *A61K 35/12* | (2015.01) |

(52) U.S. Cl.
CPC .............. *A61K 35/28* (2013.01); *A61K 35/32* (2013.01); *A61L 27/20* (2013.01); *A61L 27/3804* (2013.01); *A61L 27/3852* (2013.01); *C12N 5/0655* (2013.01); *C12N 5/0668* (2013.01); *A61K 35/12* (2013.01); *A61L 2430/06* (2013.01); *C12N 2501/115* (2013.01)

(58) Field of Classification Search
CPC .................................................. A61K 35/28
See application file for complete search history.

(56) References Cited

U.S. PATENT DOCUMENTS 5,904,716 A 5/1999 Gendler
6,365,405 B1 4/2002 Salzmann et al.

FOREIGN PATENT DOCUMENTS

WO    WO 03/024463 A1    3/2003

OTHER PUBLICATIONS

Tay et al. (2004, Tissue Engineering vol. 10(5/6), pp. 762-770). (Year: 2004).*
Ito et al. (2004, Biochem. Engineering J., vol. 20, pp. 119-125). (Year: 2004).*
Guo et al. (E-published Sep. 6, 2005, Biomaterials, vol. 26, pp. 1095-1106, print published 2006). (Year: 2006).*
Borromeo et al., "Growth Hormone Stimulates the Secretion of Insulin-like Growth Factor Binding Protein-2 (IGFBP-2) by Monolayer Cultures of Sheep Costal Growth Plate Chondrocytes", Molecular and Cellular Biochemistry, vol. 162 (1996) pp. 145-151.
Cao et al., "Transplantation of Chondrocytes Utilizing a Polymer-Cell Construct to Produce Tissue-Engineered Cartilage in the Shape of a Human Ear", Plastic & Reconstructive Surgery (1997), vol. 100 (2), pp. 297-302.
Choi et al., "Adipose Tissue Engineering Using Mesenchymal Stem Cells Attached to Injectable PLGA Spheres", Biomaterials, vol. 26 (2005) pp. 5855-5863.
Fujisato et al., "Effect of Basic Fibroblast Growth Factor on Cartilage Regeneration in Chondrocyte-Seeded Collagen Sponge Scaffold", Biomaterials, vol. 17 (1996) pp. 155-162.
Gartland et al., "In vitro Chondrocyte Differentiation Using Costochondral Chondrocytes as a Source of Primary Rat Chondrocyte Cultures: an Improved Isolation and Cryopreservation Method", Bone, vol. 37 (2005) pp. 530-544.
Guo et al., "Porous Chitosan-gelatin Scaffold Containing Plasmid DNA Encoding Transforming Grown Factor-β1 for Chondrocytes Proliferation", Biomaterials, vol. 26 (2006) pp. 1095-1106.
Hegert et al., "Differentiation Plasticity of Chondrocytes Derived from Mouse Embryonic Stem Cells", J. Cell Science, vol. 115 (2002) pp. 4617-4628.
Ito et al., "A New Methodology of Mesenchymal Stem Cell Expansion Using Magnetic Nanoparticles", Biochemical Engineering J., vol. 20 (2004) pp. 119-125.
Jager et al., "Proliferation and Osteogenic Differentiation of Mesenchymal Stem Cells Cultured onto Three Different Polymers in Vitro", Annals of Biomed. Engineering, vol. 33, No. 10 (2005) pp. 1319-1332.
Kato et al., "Sulfated Proteoglycan Synthesis by Confluent Cultures of Rabbit Costal Chondrocytes Grown in the Presence of Fibroblast Growth Factor", J. Cell Biol. (1985), vol. 100, pp. 477-485.
Martinez-Zubiaurre et al., "Behavior of Human Articular Chondrocytes During in Vivo Culture in Closed, Permeable Chambers", Cell Medicine, vol. 4 (2012) pp. 99-107.

(Continued)

*Primary Examiner* — Thaian N. Ton
*Assistant Examiner* — David A. Montanari
(74) *Attorney, Agent, or Firm* — Birch, Stewart, Kolasch & Birch, LLP

(57) ABSTRACT

The present invention relates to an artificial cartilage containing mesenchymal stem cell (MSC)-like dedifferentiated cells obtained by passage culturing costal chondrocytes, and a preparation process thereof.

5 Claims, 17 Drawing Sheets

(56) References Cited

OTHER PUBLICATIONS

Okazaki et al., "Effects of a 4.7 T Static Magnetic Field on Fetal Development in ICR Mice", J. Radiat. Res., vol. 42 (2001) pp. 273-283.
Popko et al., Rabbit Articular Cartilage Defects Treated with Cultured Costal Chondrocytes (preliminary report), Folia Morphol (Waraz), (2003), vol. 62(2), pp. 107-112.
Szeparowicz et al., "Comparison of Cartilage Self Repairs and Repairs with Costal and Articular Chondrocyte Transplantation in Treatment of Cartilage Defects in Rats", Rocz. Akad. Med. Bialymst. (2004), vol. 49 (Suppl 1), pp. 28-30.
Tay et al., "Cell Yield, Proliferation, and Postexpansion Differentiation Capacity of Human Ear, Nasal, and Rib Chondrocytes", Tissue Engineering, vol. 10, No. 5/6 (2004) pp. 762-770.
Wroblewski et al., "Inhibitory Effects of Basic Fibroblast Growth Factor on Chondrocyte Differentiation", J. Bone and Mineral Res., vol. 10, No. 5 (1995) pp. 735-742.
Zheng et al., "Material-induced Chondrogenic Differentiation of Mesenchymal Stem Cells is Material-Dependent", Exp. Therapu. Med., vol. 7 (2014) pp. 1147-1150.

\* cited by examiner

ARTIFICIAL CARTILAGE CONTAINING CHONDROCYTES OBTAINED FROM COSTAL CARTILAGE AND PREPARATION PROCESS THEREOF

CROSS-REFERENCE TO RELATED APPLICATIONS

This application is a Division of copending application Ser. No. 12/159,204 filed on Jun. 25, 2008, which is the National Phase under 35 U.S.C. § 371 of International Application No. PCT/KR2006/004479, filed on Oct. 31, 2006, which claims the benefit under 35 U.S.C. § 119(a) to Patent Application No. 10-2005-0103156, filed in Korea on Oct. 31, 2005, all of which are hereby expressly incorporated by reference into the present application.

TECHNICAL FIELD

The present invention relates to an artificial cartilage containing chondrocytes obtained from costal cartilage and a preparation process thereof.

BACKGROUND ART

Damage to articular cartilage is an exceedingly common problem affecting the joints of millions of people. The ability of adult cartilage to regenerate is limited due to avascularity and the absence of stem cell in this tissue. Although defects that extend to subchondral bone provoke the formation of a fibrous or fibrocartilagious tissue, it undergoes premature degeneration because the repair tissue is biochemically and biomechanically different from hyaline cartilage.

A variety of clinical procedures have been developed to repair articular cartilage defects, but success has been limited. Bone marrow stimulation technique (fine joint plastic surgery and drill articular plastic surgery) interpenetrate subchondral bone, and stimulate multipotent stem cells within bone marrow to repair the defects into a fibrous tissue or fibrocartilage. However, these methods have disadvantages that the repair fibrocartilage lacks such biochemical and biomechanical property as normal hyaline cartilage has. Further, their effects have not been proved yet for the large area defects, osteoarthritis and the older patient. Osteochondral/chondral graft is simple and effective for small size defect, but if the tissue is moved from low weight part to high weight part, it may cause a harmful compression due to non-physiological bearing in the transplanted position. Periosteal and perichondrial graft has a potential advantage to introduce new cell assembly which is able to construct cartilage, but has also disadvantage that hyaline-like repair tissue tends to undergo calcification through osteogenesis in cartilage.

Furthermore, several cell-based procedures using chondrocytes, mesenchymal stem cells (MSCs), periosteocytes and perichondriocytes have been developed. Chondrogenic progenitor cells such as MSCs, periosteocytes and perichondriocytes get popularity more and more as potential cell sources to repair the osteochondral defects. However, the progenitor cells capacity to construct articular chondrocytes is limited, and the age of patient is directly related to clinical results. Further, it is reported that the repair hyaline-like tissue tends to undergo calcification.

Autologous articular chondrocyte transplantation (ACT) has been clinically applied in small defects of articular cartilage, but only limited success has been reported. Even though articular chondrocytes can be easily isolated from mature articular cartilage by enzyme digestion, it requires two step-procedures for harvesting and grafting which are invasive to joint and considerably expensive. Thus ACT cannot be applied to more than two small lesions, to the lesion size larger than 10 cm$^2$, to the patient of rheumatoid or immune-related arthritis, and to the older patient due to articular cartilage degeneration with age.

Furthermore, only one to two percentage by the volume of articular cartilage is chondrocyte, in which approximately 2,000 cells/mg of human articular cartilage can be isolated for culture. An average 3 cm$^2$ defect requires 9×10$^6$ cells for the ACT procedure if implanted at cell densities similar to that found in the normal human knee joint. In reality, more cells may be required for ACT since 26% of patients under the age of 40 with grade IV chondromalacia lesions had multiple lesions. Therefore, a large number of chondrocytes are required to fill adequately a volume of defect with a similar cell density as seen in normal human articular cartilage.

During serial monolayer culture for cell expansion, chondrocytes tend to stop expressing cartilage-specific proteoglycan and type II collagen, and switch to express type I collagen with producing a small amount of proteoglycan. Such dedifferentiation is a main problem which limits cell expansion in vitro and ACT application.

Further, costal cartilage is the biggest permanent hyaline cartilage in the mammalian body, which has been suggested as a possible alternative donor source for autologous graft in reconstruction of articular cartilage, external ear and trachea. Costal cartilage has been used to repair osteochondral defects in small joint such as the interphalangeal joints and the temporomandibular joints. Costal cartilage seems to have several advantages over articular cartilage as donor tissue. Actively proliferating chondrocytes were detected even in patients 80 years of age or older, and a significant amount of costal cartilage is available in patients younger than 60 years. In addition, costal cartilage is abundant, and its easy surgical accessibility allows less harm to donor site. Therefore, if costal cartilage has the same phenotype as hyaline cartilage of articular cartilage, it can be considered the most useful source for treating a variety of articular cartilage disorders such as rheumatoid arthritis, osteoarthritis and cartilage defects of the joints.

However, so far, only autologous tissue transplantation to graft costal cartilage per se to articular cartilage part has been performed, and there has been no effort to isolate chondrocytes from costal cartilage to regenerate articular cartilage by tissue engineering method.

Furthermore, transplantation of chondrocytes or chondrogenic cells alone has shown to be successful in rabbit models, but the healing rate has limited due to loss of their viability in the transplanted cells and due to the difficulty of fixing chondrocytes in the defect. To overcome the difficulties related to the surgical procedure and to find a method of maintaining chondrocytes in the defect without outflow of the cells in the articular cavity, new approaches in different biomaterial carriers as scaffolds onto which cells are seeded, have been studied. Ideal scaffolds should be biocompatible, bioabsorbable or remodeled, and provide framework that facilitates new tissue growth. They should also display material and mechanical properties compatible with articular cartilage function. A variety of biomaterials, naturally occurring such as collagen-based biomaterial; collagen type I and II or collagen/glycosaminoglycan (GAG) composites and synthetic such as polyglycolic acid (PGA) and polylactic acid (PLLA), or their composite mixture, PLGA (poly D,L-lactic-co-glycolic acid), have been introduced as potential cell-carrier substances for cartilage repair. They have shown that cartilage-specific extracellular matrix (ECM) components such as type II collagen and GAG play a critical role in regulating expression of the chondrocytic phenotype and in supporting chondrogenesis both in vitro and in vivo.

Chitosan is the alkaline de-acetylated product of chitin and a family of poly-D-glucosamine units that vary in their degree of deacetylation and molecular weight. Many investigators suggested that chitosan might be considered as a structural biomaterial for the repair of connective tissues because of its structural similarity to GAGs found in the extracellular matrix. Chitosan and some of its degraded products can be involved in the synthesis of the articular liquid components such as chondroitine, chondroitine-sulfate, dermatane-sulfate, keratane-sulfate and hyaluronic acid (HA). These substances are necessary for nutrition of the cartilage. The fact that chitosan is polycationic, and its structure is similar to hyaluronic acid which is an important molecule of ECM of articular cartilage has a particular importance for cartilage tissue engineering. Use of chitosan-based matrices in the tissue engineering of hyaline cartilage has been recently reviewed. Lahiji et al. (2000) showed that chondrocytes which are cultured on chitosan films maintain differentiated phenotype and express cartilage specific ECM proteins such as type II collagen and sulfated proteoglycan. Studies exploring the use of chitosan to potentiate neochondrogenesis have shown the ability of chitosan to promote the maintenance of the chondrocyte phenotype and biosynthesis of cartilage specific ECM components when grown on chitosan films (Lahiji et al, 2000). Chitosan has also been shown to potentiate the differentiation of osteoprogenitor cells and may have also enhanced bone formation.

Hyaluronic acid plays a vital role in many biological processes such as tissue hydration, proteoglycan (PG) organization in the ECM, and cell differentiation. It is also a component of healthy articular cartilage. Patti et al. (2001) showed that HA improved in vitro substrate adhesion ability and proliferative activity of human cartilage cells. HA also improved clinical function in early arthritis (Patti et al., 2001).

Further, fibroblast growth factor (FGF) is a strong mitogen for connective tissue cells and MSCs (J. Cell Biol. 100, 477-485, 1985). During cell expansion, FGF inhibits the formation of thick F-actin structure to maintain chondrogenic potential of articular chondrocytes (Exp. Cell Res. 253, 681-688, 1999). Also, FGF is known to maintain multifamily differentiation of MSC throughout numerous mitoses.

SUMMARY OF THE INVENTION

First, the present inventors have studied whether chondrocytes obtained from costal cartilage can be used as cell source for tissue engineered artificial cartilage. Also, they have studied a way to solve the problem that chondrocytes tend to lose chondrocytic phenotype because of dedifferentiation during the passage. Further, they have continued to evaluate whether chitosan-based scaffolds onto which costal chondrocytes are seeded can be used for articular cartilage regeneration.

As a result, they discovered that chondrocytes obtained from costal cartilage are better than those from articular cartilage as donor cell source for cartilage repair. Also, they discovered that dedifferentiated chondrocytes during the passage show MSC properties to confirm their ability for use as cell therapeutic agent as well as artificial cartilage, by redifferentiating them into desired cells in the differentiation inducible medium. In addition, the present inventors confirmed that chondrocytes-loaded chitosan-based scaffolds when transplanted to articular defects show effective articular regeneration, to complete the present invention.

Thus, the object of the present invention is to provide an artificial cartilage containing MSC-like dedifferentiated cells obtained by passaging costal chondrocytes and a preparation process thereof.

DISCLOSURE OF THE INVENTION

Figure 1:
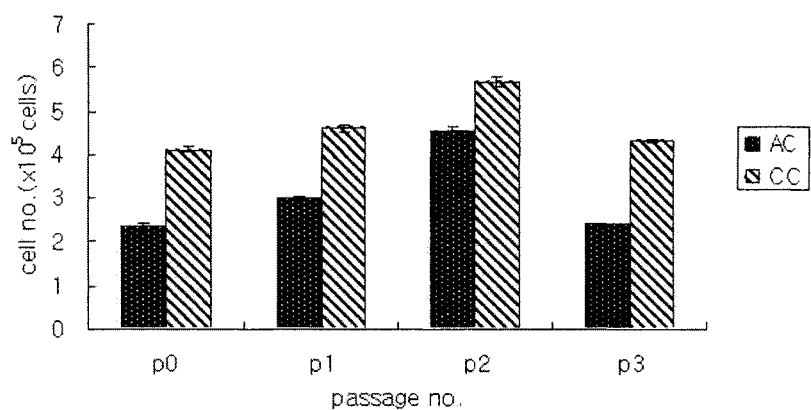
FIG. 1 is a graph showing comparison of in vitro cell expansion ability between articular chondrocytes (ACs) and costal chondrocytes (CCs).

First, the present invention relates to an artificial cartilage containing MSC-like dedifferentiated cells obtained by passaging costal chondrocytes. It is preferable that the costal chondrocytes are passaged in MSC growth medium (MSCGM), in particular fibroblast growth factor (FGF)-containing MSCGM for better cell expansion and differentiation into cartilage.

Second, the present invention relates to an artificial cartilage containing redifferentiated chondrocytes obtained by culturing the MSC-like dedifferentiated cells in chondrogenic medium. In one embodiment, the MSC-like dedifferentiated cells are pellet cultured in chondrogenic medium.

Third, the present invention relates to an artificial cartilage wherein chondrocytes are loaded on chitosan-based scaffold. The chitosan-basaed scaffold is preferably selected from the group consisting of chitosan sponge; Transforming Growth Factor-β (TGF-β) containing chitosan sponge; hyaluronic acid (HA)-coated chitosan sponge; chondroitine-sulfate-coated chitosan sponge; and chitosan-collagen composite sponge. More preferably, the chitosan-basaed scaffold is HA-coated chitosan sponge or HA-coated chitosan-collagen composite sponge.

Fourth, the present invention relates to a process for preparing an artificial cartilage comprising a step of passaging costal chondrocytes to obtain MSC-like dedifferentiated cells. In one embodiment, the costal chondrocytes are passaged in MSCGM or FGF-containing MSCGM. In another embodiment, the MSC-like dedifferentiated cells obtained by passaging costal chondrocytes are redifferentiated by culturing them in chondrogenic medium, preferably by pellet culturing in chondrogenic medium. In another embodiment, the process includes a step of loading the MSC-like dedifferentiated cells on chitosan-based scaffold.

Fifth, the present invention relates to a cell therapeutic agent containing MSC-like dedifferentiated cells obtained by passaging costal chondrocytes. In one embodiment, the cell therapeutic agent contains redifferentiated chondrocytes obtained by culturing the MSC-like dedifferentiated cells in chondrogenic medium. In another embodiment, the cell therapeutic agent contains osteoblasts obtained by culturing the MSC-like dedifferentiated cells in osteogenic medium. In another embodiment, the cell therapeutic agent contains adipocytes obtained by culturing the MSC-like dedifferentiated cells in adipogenic medium.

Below, the present invention is explained in more detail.

The main technical limitation in ACT for articular cartilage repair is that a donor cartilage without weight-bearing in knee joint has low cell growth capacity, and it is difficult to obtain adequate number of chondrocytes for covering cartilage defect according to dedifferentiation of chondrocytes during in vitro cell expansion. In addition, success of ACT application is restricted by the patient age and narrow choice of donor site.

Thus, in the present invention, it was first estimated whether costal cartilage which maintains a longer growth capacity during its existence and has a larger donor tissue in human body can be applied as donor cell source for ACT. First, based on initial cell yield, cell expansion rate and dedifferentiation, it was evaluated whether chondrocytes isolated from costal cartilage can be applied as a potential cell source for tissue engineered articular cartilage. Particularly, in the present invention, initial cell yield and cell expansion rate in monolayer culture of chondrocytes obtained from costal cartilage are compared to those of chondrocytes from articular cartilage. In addition, dedifferentiation rate during in vitro cell culture is estimated by cell morphology and type II collagen expression.

As a result, costal cartilage gave 2.6 folds higher initial cell yield than articular cartilage. During in vitro cell culture, costal chondrocytes (CCs) more rapidly grew, and gave about 3.0 folds higher cell expansion up to P4 than articular chondrocytes (ACs). During serial culture, ACs and CCs gradually lost their chondrocytic phenotype but instead converted into fibroblast-like cells, and type II collagen expression decreased. The loss of their original phenotype was more expedited in CCs than ACs. Comparing the same number of passage, CCs more rapidly dedifferentiated than ACs.

The results of first culture represented by comparison of ACs and CCs from the same rabbit which have dedifferentiation and growth profile according to in vitro cell expansion passage suggest that costal cartilage can be used as potential cell source for osteoarthritis repair.

In further study, the present inventors confirmed that dedifferentiated cells obtained by passaging costal cartilage have MSC properties. MSC is chondrogenic progenitor cells, and has a meaning as potential cell source for repairing osteochondral defect. Thus, in the present invention, it was first disclosed that MSC-like dedifferentiated cells obtained from costal chondrocytes are chondrogenic progenitor cells which can be used for osteochondral defect repair.

MSC-like dedifferentiated cells according to the present invention were able to differentiate into osteoblasts and adipocytes as well as chondrocytes. Thus, in the present invention, the term "MSC-like dedifferentiated cells" refers to cells which are dedifferentiated by passage and have potential to differentiate into chondrocytes, osteoblasts, adipocytes, etc., like MSC. That is, the term refers to multipotent cells.

In further study, the present inventors disclosed that when costal chondrocytes are passaged in, in particular FGF-containing MSCGM, the cell expansion rate is outstanding, and differentiation into chondrocytes is excellent. It is anticipated that normal cell culture medium containing DMEM may have the same result if FGF is added thereto.

Furthermore, in the present invention, as scaffold for loading chondrocytes, chitosan-based scaffold, in particular sponge form HA-coated chitosan scaffold was used to estimate the role of cultured autologous costal chondrocytes laden HA-coated chitoan composite scaffold in the repair of full-thickness articular cartilage defects in a weight-bearing site in animal model. The use of the rabbit knee model in assessment of cartilage repair has been widely used, and spontaneous healing of full-thickness 3 mm-diameter chondral defects in the rabbit patellar groove has been reported to occur within 6 to 8 weeks in 4 to 6 months old rabbit. Thus, this period is needed to reveal most degenerative failures of the apparently healed carilage. In the designed animal model experiment as below (4 mm diameter osteochondral defect), it was shown that autologous costal chondrocytes within chitosan-based scaffold according to the present invention very effectively repaired full-thickness articular cartilage defects in a weight-bearing site.

Hereinafter, the present invention will be described in more detail with reference to the following Examples, but the scope of the present invention should not be construed to be limited thereby in any manner.

EXAMPLES

Example 1: Evaluation on Whether Costal Chondrocytes can be Donor Cell Source for Articular Cartilage Repair Materials and Methods Isolation of Chondrocytes Articular and costal cartilages were obtained from 3 to 4 months old New Zealand White Rabbit, and then weighed. To harvest costal cartilage, animals were anesthetized by intravenous injection of a mixture of xylazine hydrochloride (2 mg/weight kg, Rompun, Bayer, Korea) and ketamine hydrochloride (6-10 mg/weight kg, ketalar, Yuhan Co., Korea). The skin in the region of the chest was shaved, washed with alcohol, and prepared with povidone-iodine solution. The back side of the right chest was opened, and $9^{th}$ and $10^{th}$ costal cartilages were exposed. The costal cartilages, after removing soft adhering tissues, were then weighed. These cartilages were minced into 1-2 $mm^3$ pieces and rinsed 3 times in D-PBS (Dulbecco's phosphate buffered saline; Jeil Biotech services Inc., Taegu, Korea). After being rinsed, the minced cartilage was digested by the enzyme cocktail solution including collagenase D (2 mg/ml, Roche Diagnostic GmbH, Germany), hyaluronidase (1 mg/ml, Roche), and DNase (0.75 mg/ml, Roche) under 37° C. and 5% $CO_2$ for overnight. Then the solution was filtered through a 53 μm nylon mesh, isolated cells were washed 2 times with DMEM (Dulbecco's Modified Eagle Medium; Gibco Life Technologies, Grand Island, N.Y., U.S.A.) supplemented with 10% fetal bovine serum (FBS; Hyclone technologies, U.S.A.) and 1% penicilline/Streptomycin/Fungizone cocktail (Gibco), and viable cells were counted on Haemocytometer based on the trypan blue exclusion. The cells were plated at a cell density of $5 \times 10^5$ cells/100 mm diameter Petri dish, the culture medium was changed every other day, and fresh 50 μg/ml L-ascorbic acid (Sigma, St. Louis, Mo., U.S.A.) was added at each medium change. The primary cells at confluence were subcultured up to P4.

MTT Assay

For MTT assay, ACs and CCs at each passage were seeded at cell density of $1 \times 10^5$ cells per well of 6-well culture plate and cultured for 5 days. The cell growth was determined based on MTT assay (Mosman T. Rapid colormetric assay for cellular growth and survival, application to proliferation and cytotoxicity assays, J. Immunol. Methods 1983; 65: 55-63). For the calibration of cell number from optical density (O.D.), standard curve was measured in the range of 1 to $8 \times 10^5$ cells and O.D. was transformed to the cell number.

Immunofluorescence Staining of Type II Collagen

For immunofluorescence staining, the chondrocytes from each passage were plated onto cover slip, cultured for 2 days, fixed with 3.7% formalin in PBS for 10 minutes, and permeabilized with 0.2% Triton X-100 in PBS. The permeabilized cells were incubated with 20% normal goat serum to block nonspecific reaction and a monoclonal anti-type II collagen antibody (monoclonal anti-mouse antibody; Chemicon international Inc., Temecula, Calif., U.S.A.) was used as a primary antibody. Fluorescein isothiocyanate (FITC) labeled goat anti-mouse IgG conjugate (Vector Lab., Burlingame, Calif., U.S.A.) was used as a secondary antibody, and the cover slip was incubated for 5 minutes with 4',6-diamidino-2-phenylindole (DAPI; 1 g/ml; Sigma Chemical Co., St. Louis, Mo., U.S.A.) for nuclear staining. Cells were observed under fluorescence microscope (Olympus Optical Co., Japan).

Statistics

Statistical analysis was carried out by the unpaired t test to determine whether variables were significantly different ($p < 0.05$) in the each experiment.

Results

Comparison of Initial Cell Yield and Cell Expansion Rate of Chondrocytes Isolated from Articular Cartilage and Costal Cartilage In order to search potential donor site suitable for autologous chondrocytes transplantation in adult, the cell yield of chondrocytes isolated from articular cartilage and costal cartilage are compared (Table 1).

TABLE 1

Comparison of initial cell yield of chondrocytes isolated from articular cartilage and costal cartilage

|    | 1 | 2 | 3 | Mean (cells/mg) ± S.D. |
|----|---|---|---|---|
| AC | 6,000 | 7,000 | 13,400 | 8,800 ± 3,278[a] |
| CC | 20,000 | 26,600 | 22,100 | 22,900 ± 2,753 |

[a]Mean value ± S.D. from three independent cell isolations. Statistical analysis was carried out by the student t-test (p < 0.05).

As shown in Table 1 above, the articular cartilage and the costal cartilage gave initial cell yields of 8,800±3,278 cells/mg and 22,900±2,753 cells/mg, respectively, which corresponds approximately 2.6 folds higher cell yield in the costal cartilage than in the articular cartilage. Thus, costal cartilage seems to be the better donor site for autologous chondrcocytes than articular cartilage in terms of initial cell yield.

Then, in vitro expandability of chondrocytes from articular cartilage or costal cartilage was compared. The cells from each passage were separately plated at a density of $1 \times 10^5$ cells per well of 6-well plate and MTT assay was performed at 5th day after seeding (FIG. 1). Throughout the cell passages, overall growth rates of CCs were higher than those of ACs. At P0, the growth rate of CCs was approximately twice than that of ACs. At P2, the growth rate of ACs was similar to that of CCs, but at P3, the growth rate decreased than P2.

For the estimation of expandability of chondrocytes isolated from articular cartilage and costal cartilage, the time to reach confluence and total cell number at each cell passage were compared after seeding the same cell numbers (Table 2).

TABLE 2

Comparison of time to reach confluence and total cell expansion rate at confluence between ACs and CCs

|    | P0 to P2 | | P0 to P4 | |
|----|---|---|---|---|
|    | Time (days) | Expansion rate (folds) | Time (days) | Expansion rate (folds) |
| AC | 20 ± 7[a] | 22 ± 8.4 | 37 ± 7.3 | 106 ± 22 |
| CC | 13 ± 3 | 54 ± 14.5 | 29 ± 3.4 | 310 ± 70 |

[a]Mean value ± S.D. from three independent experiments.

As shown in Table 2 above, in the aspect of the cell expansion advantage in vitro, CCs seem the better donor chondrocytes than ACs.

Figure 2:
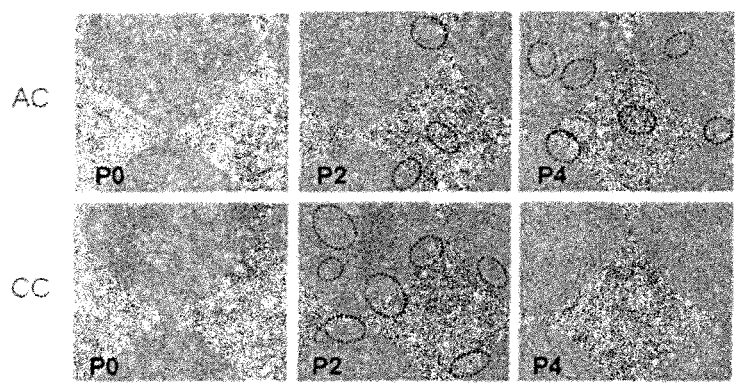
FIGS. 2 and 3 are pictures showing the morphological change and type II collagen expression of ACs and CCs at each passage.
Figure 3:
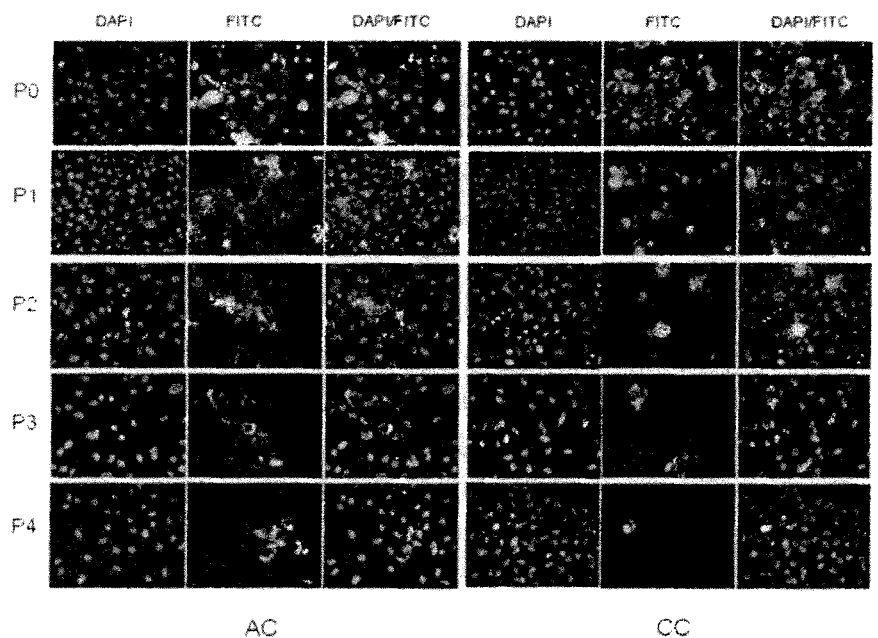

Comparison of the Loss of Chondrocytic Phenotype of Articular Chondrocytes with Costal Chondrocytes during in vitro Expansion During in vitro cell expansion, chondrocytes frequently lose their in vivo properties such as round shape, type II collagen and GAG expression. Both morphological changes and expression of type II collagen were examined at each passage of ACs and CCs (FIGS. 2 and 3). From P2, some group of cells began to lose their original round but instead converted into fibroblastic spindle shape (FIG. 2). At P4, most CCs actually changed their morphologies into fibroblastic phenotype. However, this morphological change was much slower in ACs than CCs. Thus, ACs more slowly expand in vitro than CCs, and more slowly changes their morphology during in vitro cell expansion than CCs.

For further confirmation on whether fibroblastic morphological change is accompanied by the loss of type II collagen expression, immunofluorescence staining was performed with anti-type II collagen antibody (FIG. 3). At P0, 99% cells of primary chondrocytes derived either from costal cartilage or articular cartilage expressed type II collagen. At P2, the number of chondrocytes expressing type II collagen rapidly decreased, and this was much severer in CCs. At P4, most CCs did not express type II collagen, whereas some of ACs maintained expressing type II collagen.

The number of type II collagen expressing cells was counted among DAPI positive chondrocytes (Table 3).

TABLE 3

Number of type II collagen expressing cells at different cell passage (%)

|    | AC (%)        | CC (%)       |
|----|---------------|--------------|
| P0 | 98.6 ± 1.1[a] | 97.2 ± 2.4   |
| P1 | 53.5 ± 7.8    | 37.6 ± 5.4   |
| P2 | 23.6 ± 4.6    | 10.0 ± 3.3   |
| P3 | 14.3 ± 3.0    | 5.1 ± 0.7    |
| P4 | 10.4 ± 2.8    | 1.0 ± 0.4    |

[a]Mean value ± S.D.

to As shown in Table 3 above, chondrocytes gradually lost their original phenotype such as round cell morphology and type II collagen expression capacity during in vitro expansion, which was much faster in CCs than ACs.

Example 2: Confirmation on Whether Fully Dedifferentiated Costal Chondrocytes Show MSC's Properties Materials and Methods Isolation of Chondrocytes Costal cartilages were obtained from 4 to 5 months old New Zealand White Rabbit. The skin in the region of the chest was shaved, washed with alcohol, and prepared with povidone-iodine solution. The back side of the right chest was opened, and 9$^{th}$ and 10$^{th}$ costal cartilages were exposed. The costal cartilages, after removing soft adhering tissues, were then weighed. These cartilages were minced into 1-2 mm$^3$ pieces and rinsed 3 times in D-PBS (Dulbecco's phosphate buffered saline; Jeil Biotech services Inc., Taegu, Korea). After being rinsed, the minced cartilage was digested by the enzyme cocktail solution including collagenase D (2 mg/ml, Roche Diagnostic GmbH, Germany), hyaluronidase (1 mg/ml, Roche), and DNase (0.75 mg/ml, Roche) under 37° C. and 5% $CO_2$ for overnight. Then the solution was filtered through a 53 μm nylon mesh, isolated cells were washed 2 times with DMEM (Dulbecco's Modified Eagle Medium; Gibco Life Technologies, Grand Island, N.Y., U.S.A.) supplemented with 10% fetal bovine serum (FBS; Hyclone technologies, U.S.A.) and 1% penicilline/Streptomycin/Fungizone cocktail (Gibco), and viable cells were counted on Haemocytometer based on the trypan blue exclusion. The cells were plated at a cell density of $5 \times 10^5$ cells/100 mm diameter Petri dish, the culture medium was changed every other day, and fresh 50 μg/ml L-ascorbic acid (Sigma, St. Louis, Mo., U.S.A.) was added at each medium change. The primary cells at confluence were subcultured up to P7.

Expression of Type I, II Collagen and Smooth Muscle Actin (SMA) Antibody

The costal chondrocytes at P7 were plated onto cover slip, cultured for 2 days, fixed with 3.7% formalin in PBS for 10 minutes, and permeabilized with 0.2% Triton X-100 in PBS. Anti-type I collagen antibody (polyclonal anti-goat antibody: southern), anti-type II collagen antibody (monoclonal anti-mouse antibody: Chemicon international Inc., Temecular, U.S.A.) or anti SMA antibody (monoclonal anti-mouse antibody: DAKO) were applied to the specimen for overnight at 4° C., incubated with secondary antibody, then incubated with streptavidin-peroxidase for 1 hour, and developed with 0.1% 3,3'-diaminobenzidine tetrahydrochloride (DAB; Chromogen, DAKO Corp., Calif., U.S.A.) in PBS for 5 minutes. Fast red dye (Vector Lab., Burlingame, Calif., U.S.A.) was used for counterstaining.

Results

Figure 4:
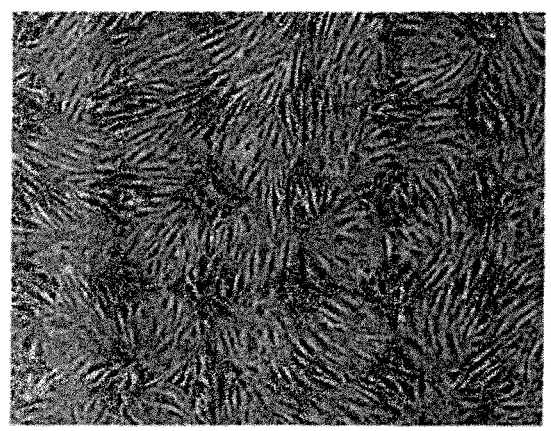
FIG. 4 is a picture showing CCs morphology at P7.
Figure 5:
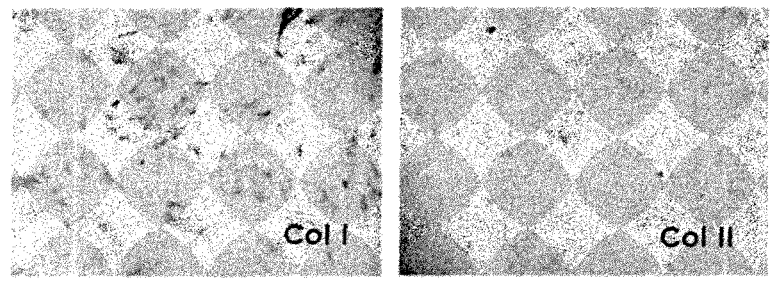
FIGS. 5 and 6 are pictures showing type I and II collagen and smooth muscle actin (SMA) antibody expression.
Figure 6:
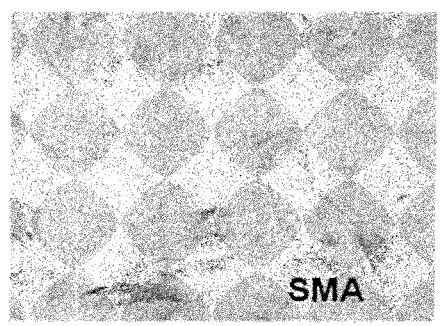

Confirmation on Dedifferentiation of Costal Chondrocytes and Expression of MSC's Properties As shown in FIG. 4, costal chondrocytes at P7 lost their original round shape but instead converted into fibroblastic spindle shape. This shows that costal chondrocytes fully dedifferentiated. FIGS. 5 and 6 show type I, II collagen and SMA antibody expression in dedifferentiated chondrocytes. In every cell, type I collagen is still expressed, but type II collagen is not expressed at all. One of the characteristics of MSC, expression of SMA was observed in many cells (FIG. 6). As above, the expression of type I collagen and SMA confirmed that passaged costal chondrocytes show MSC's properties.

Example 3: Evaluation on Expansion of Costal Chondrocytes and their Differentiation into Cartilage According to Culture Condition (DMEM+10% FBSs, MSCGM or FGF-Containing MSCGM)

Materials and Methods

Isolation and Culture of Chondrocytes

Chondrocytes were isolated by the method as described above, and viable cells were counted on Haemocytometer based on the trypan blue exclusion. The chondrocytes were plated at a cell density of $5 \times 10^5$ cells/100 mm diameter Petri dish, and cultured in DMEM (DMEM-FBS), MSCGM (Cambrex Bio Science Walkersville, Inc., MD, U.S.A.), or MSCGM added with 1 ng/ml of FGF (R&D System Inc., MN, U.S.A.).

Cell Expansion Rate According to the Medium

When the dish was filled with the cells, the cells were removed by Trypsin-EDTA (Gibco), and viable cells were counted on Haemocytometer based on the trypan blue exclusion to evaluate cell expansion rate. Then, the cells were plated at a cell density of $5 \times 10^5$ cells/100 mm diameter Petri dish, and cultured in the same medium.

Expression of Type I and II Collagen and SMA Antibody

The costal chondrocytes cultured in DMEM-FBS, MSCGM or MSCGM-FGF at each passage were plated onto cover slip, cultured for 2 days, fixed with 3.7% formalin in PBS for 10 minutes, and permeabilized with 0.2% Triton X-100 in PBS. The permeabilized cells were incubated with 20% normal goat serum to block nonspecific reaction, and anti SMA antibody (monoclonal anti-mouse antibody: DAKO) was used as a primary antibody and applied to the specimen for overnight at 4° C. Fluorescein isothiocyanate (FITC) labeled goat anti-mouse IgG conjugate was used as a secondary antibody, and the cover slip was incubated for 5 minutes with 4',6-diamidino-2-phenylindole (DAPI; 1 g/ml; Sigma Chemical Co., St. Louis, Mo., U.S.A.) for nuclear staining. Cells were observed under fluorescence microscope (Olympus Optical Co., Japan).

After washing the bottom of the Petri dish 2 times with PBS, the costal chondrocytes cultured in DMEM-FBS, MSCGM or MSCGM-FGF at each passage were dissolved with cell dissolving buffer (Biolabs; 20 mM Tris-HCl pH 7.4, 150 mM NaCl, 1 mM Na2EDTA, 1 mM EGTA, 1% Triton, 2.5 mM sodium pyrophosphate, 1 mM $Na_3VO_4$, 1 mM beta-glycerophosphate, 1 ug/ml leupeptin) added with 2 mM of phenylmethylsulfonylfluoride (PMSF) for inhibiting protein degradation enzyme activity, and centrifuged to obtain the supernatant for the use for collagen isolation. The proteins were loaded to 10% SDS-PAGE, transferred into membrane, and performed western blotting with anti-type I collagen antibody and anti-type II collagen antibody (polyclonal anti-goat antibody: southern).

Differentiation Induction into Chondrocytes

The costal chondrocytes expanded up to P7 or P8 in DMEM-FBS, MSCGM or MSCGM-FGF were made into pellet, and induced to differentiate into cartilage in chondrogenic medium for 3 weeks. Safranin-O staining was performed to estimate the degree of differentiation into cartilage.

Results

Cell Expansion Rate Depending on the Medium

When the cells filled the dish, the cells were removed by Trypsin-EDTA (Gibco), and viable cells were counted on Haemocytometer based on the trypan blue exclusion to evaluate cell expansion rate.

Figure 7:
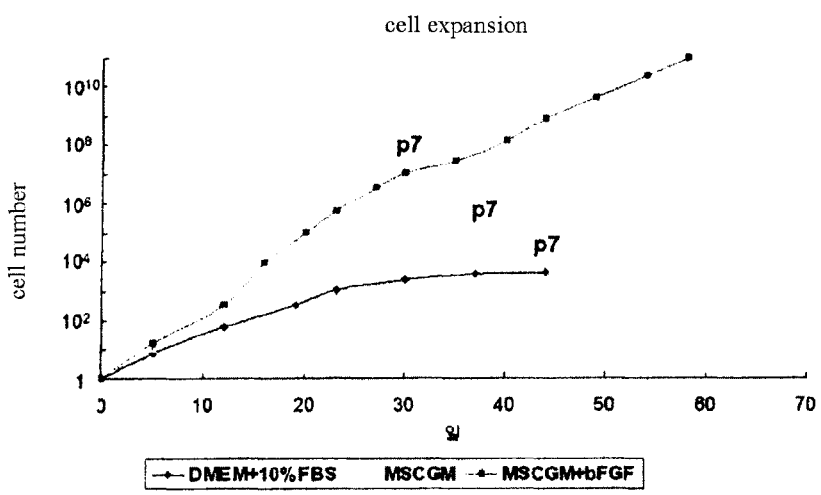
FIG. 7 is a graph showing cell expansion rate in DMEM-FBS, MSCGM and MSCGM-FGF.

As shown in FIG. 7, to arrive up to P7, it took about 30 days in MSCGM-FGF wherein the cells expanded about $10^7$ folds, and it took about 38 days in MSCGM where the cells expanded about $10^5$ folds. However, in DMEM-FBS, in about a month, cell expansion was hardly occurred with showing a graph in parabolic shape, and at P7, the cell expanded about $10^3$ folds only.

Thus, in the culture of costal chondrocytes, the expansion rate of costal chondrocytes was better in MSCGM than in DMEM+10% FBS. In addition, when cultured in MSCGM added with FGF, the expansion rate of costal chondrocytes was outstandingly superior. It can be anticipated that the same result would be obtained if the costal chondrocytes are cultured in DMEM added with FGF.

Expression of Type I and II Collagen and Anti-SMA Antibody

The expression degree of type I and II collagen and anti-SMA antibody was measured for the costal chondrocytes cultured in DMEM-FBS, MSCGM or MSCGM-FGF.

Figure 8:
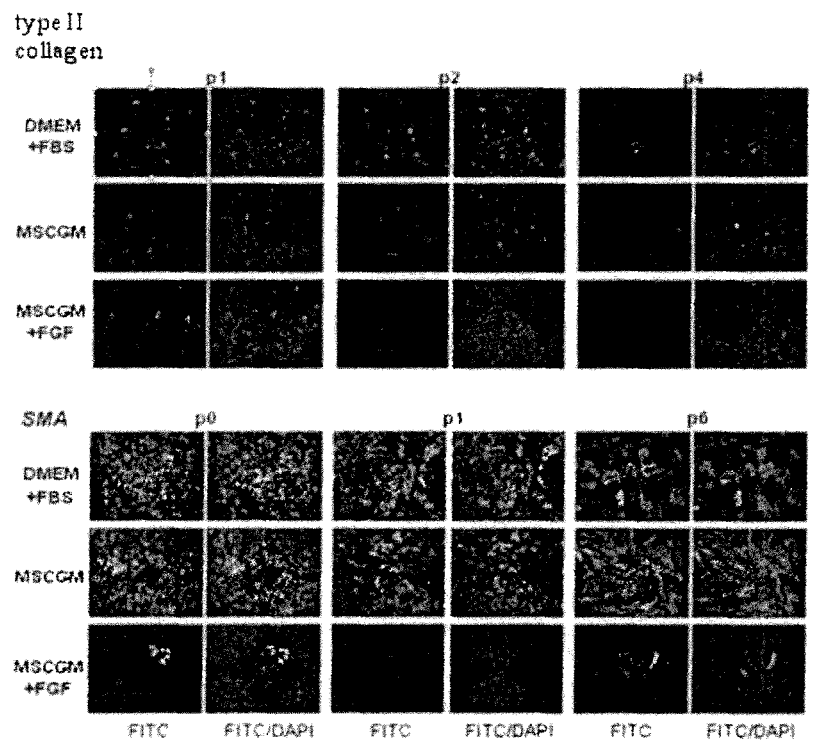
FIGS. 8 and 9 are pictures showing type I collagen, type II collagen and SMA antibody expression of the cells cultured in DMEM-FBS, MSCGM and MSCGM-FGF, respectively.

As shown in FIG. 8, type II collagen expression decreased as the passage increase, and the decreasing rate of type II collagen expression by costal chondrocytes was higher in the order of MSCGM-FGF, MSCGM and DMEM-FBS.

In costal chondrocytes expanded in MSCGM and DMEM-FBS, the SMA expressing cells were about 90%, namely, many cells expressed SMA. However, in costal chondrocytes expanded in MSCGM-FGF, very small number of cells expressed SMA over passages.

Figure 9:
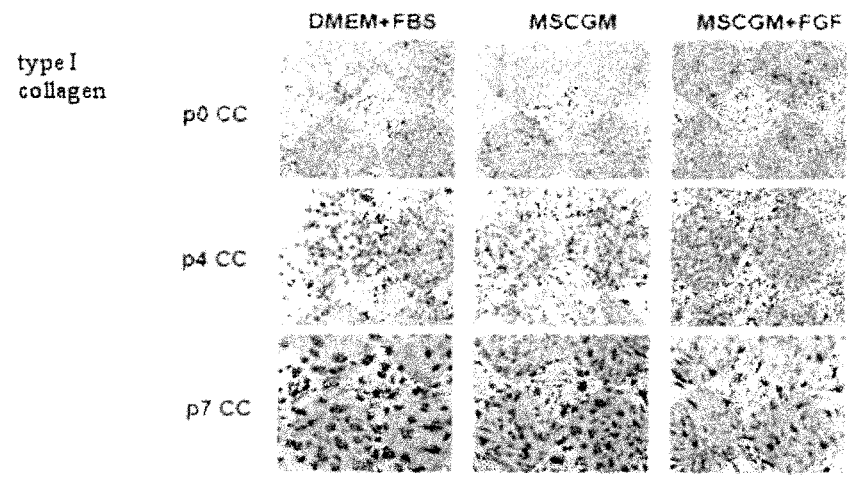

As shown in FIG. 9, in costal chondrocytes expanded in DMEM-FBS and MSCGM, the type I collagen expression increased as the passage increase, and at P7, almost all the cells expressed type I collagen. In contrast, only 60 to 70% of the cells expanded in MSCGM-FGF expressed type I collagen.

Expression of GAG

Figure 10:
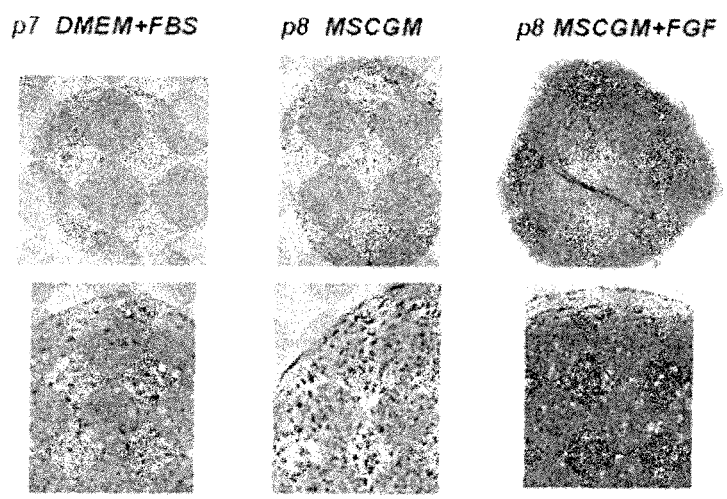
FIG. 10 shows the results of Safranin-O staining for GAG to confirm differentiation of the cells cultured in DMEM-FBS, MSCGM and MSCGM-FGF into chondrocytes.

As shown in FIG. 10, the costal chondrocytes expanded in DMEM-FBS show GAG expression mainly at the outer wall of the pellet, and most cells in the outer wall show chondrocytic morphology in the high powered microscopic picture. The costal chondrocytes expanded in MSCGM show low GAG expression in some of the pellet surface after 3 weeks cartilage differentiation, and very small number of cells shows chondrocytic morphology. In contrast, the cells expanded in MSCGM-FGF show strong GAG expression in most pellets after 3 weeks cartilage differentiation, and show chodrocytic morphology.

Consequently, when MSCGM added with 1 ng/ml of FGF is used as culture medium for expanding costal chondrocytes, chondrocytic differentiation capacity is maintained after cell expansion of about $2 \times 10^7$ folds.

Example 4: Redifferentiation of Fully Dedifferentiated Costal Chondrocytes

Materials and Methods

Isolation of Chondrocytes

The dedifferentiated cells cultured up to P7 in the Example 2 were used.

Differentiation of Fully Dedifferentiated Costal Chondrocytes into Chondrocytes

For redifferentiation of the fully dedifferentiated costal chondrocytes into chondrocytes, the cells were inoculated $1 \times 10^6$ cells/15 ml tube, and pellet cultured. The medium was changed to chondrogenic medium (High glucose DMEM, 1% ITS+3 (Sigma), 100 nM dexamethasone (Sigma), 50 ug/ml vit C (Sigma), 40 ug/ml praline (Sigma), 10 ng/ml TGF $\beta_3$ (R&D system, Inc., MN, U.S.A.), and the control group was filled with basal medium (DMEM-HG, 10% FBS). The medium was changed 2 times a week, and observed at 2 and 3 weeks.

To confirm differentiation into chondrocytes, at 2 and 3 weeks, 3-D constructs were fixed with 3.7% phosphate-buffered formalin, prepared to paraffin specimen, and sectioned by 5 μm thickness. The thin sections were deparaffinized and stained with Safranin-O and fast green (Sigma) for observing GAG distribution.

Differentiation of Fully Dedifferentiated Costal Chondrocytes into Osteoblasts

For redifferentiation into osteoblasts, the costal chondrocytes at P7 were inoculated at a cell density of $2 \times 10^4$ cells/cm² 6 well and 24 well, and cultured in osteogenic medium (DMEM, 10% FBS, 100 nM dexamethasone (Sigma), 10mM β-glycerol phosphate (Sigma), 50 ug/ml vit C (Sigma)). The medium was changed 2 times a week, and observed at 2 and 3 weeks. The basal medium (DMEM, 10% FBS) was used for the control group.

To confirm differentiation into osteoblasts, the cells were stained with Alkaline phosphatase as differentiation initial marker. The degree of expression was histochemically observed with Alkaline phosphatase measurement kit (SIGMA-ALDRICH, St. Louis, Mo., U.S.A.). Also, the cells were stained with Alizarin Red S (SIGMA-ALDRICH) which stains mineral components secreted during osteoblasts maturation, to observe the degree of differentiation into osteoblasts.

Differentiation of Fully Dedifferentiated Costal Chondrocytes into Adipocytes

For redifferentiation into adipocytes, the costal chondrocytes at P7 were inoculated at a cell density of 2×10⁴ cells/cm² 6 well and 24 well, and cultured in adipogenic medium (High glucose DMEM (Gibco), 10% FBS, 10 mg/ml insulin (Sigma), 100 nM dexamethasone (Sigma), 0.2 mM indomethacin (Wako Pure Chemical Industries, Japan), 500 uM 3-isobutyl-1-methylxanthin (Wako)) for 3 days, and repeated with 1 day culture in adipogenic medium (High glucose DMEM, 10% FBS). The basal medium (DMEM-HG, 10% FBS) was used for the control group, and observed at 2 and 3 weeks.

To confirm differentiation into adipocytes, the cells were stained with Oil Red O which particularly stains lipid droplets.

Results

Differentiation into Chondrocytes

Figure 11:
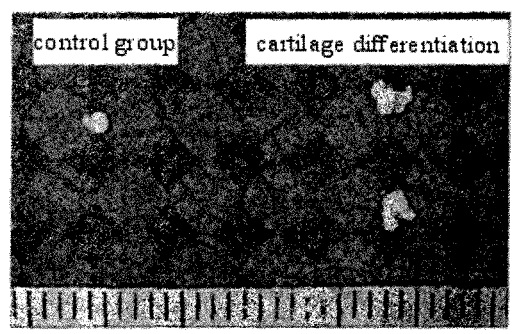
FIG. 11 shows the results of redifferentiation of costal chondrocytes at P7 into cartilage in pellet form in cartilage differentiation medium.

FIG. 11 shows a macroscopic picture of the results at 3 weeks of differentiation induction of costal chondrocytes at P7 into chondrocytes. The cells one another formed the pellet, and the size of the pellet was bigger in cartilage induction group compared to the control group (basal medium: DMEM, 10% FBS).

Figure 12:
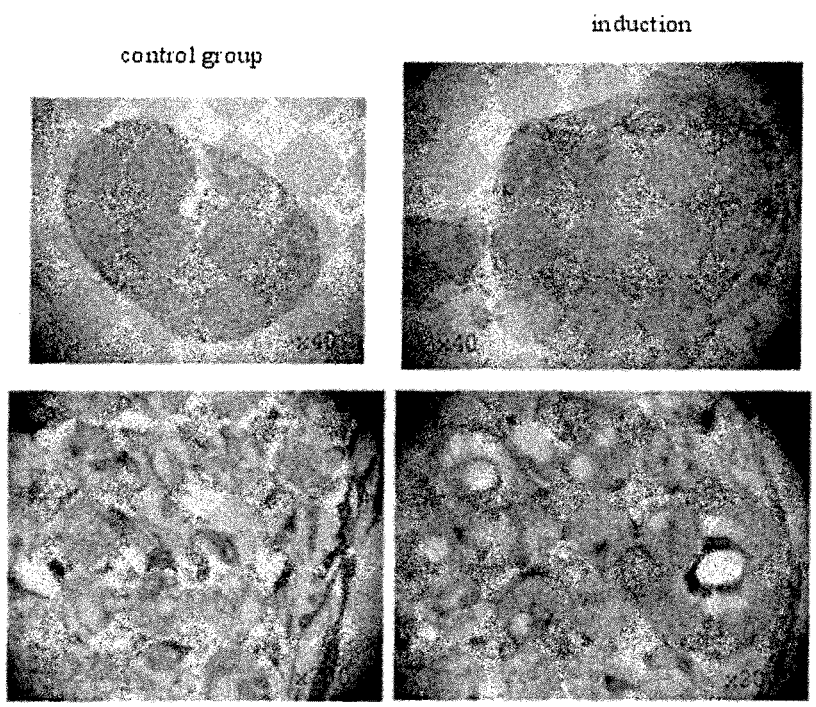
FIG. 12 shows the results of Safranin-O staining for GAG to confirm differentiation into chondrocytes.

FIG. 12 shows the results of Safranin-O staining for GAG. At 3 weeks of differentiation induction, GAG expression was observed in the outer wall of the pellet. The cells show chondrocytic morphology. The control group did not express GAG, nor show chondrocytic morphology.

Differentiation into Osteoblasts

Figure 13:
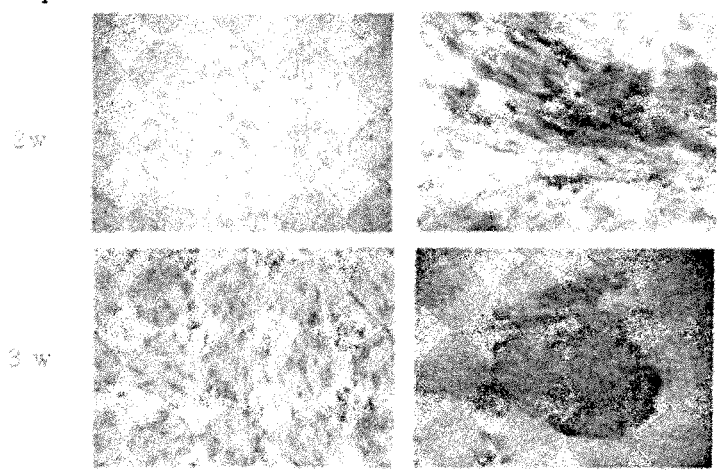
FIG. 13 is a picture showing Alkaline phosphatase expression as osteogenic differentiation initial marker in the cells which are induced to be differentiated into osteoblasts.

To confirm differentiation into osteoblasts, Alkaline phosphatase activity was observed. FIG. 13 is a picture showing Alkaline phosphatase measurement by using Alkaline phosphatase measurement kit (SIGMA-ALDRICH, St. Louis, Mo., U.S.A.). Alkaline phosphatase activity, as osteogenic differentiation initial marker, strongly expressed at 2 weeks of differentiation, and tends to decrease a little at 3 weeks. The control group cultured in basal medium did not express Alkaline phosphatase activity.

Figure 14:
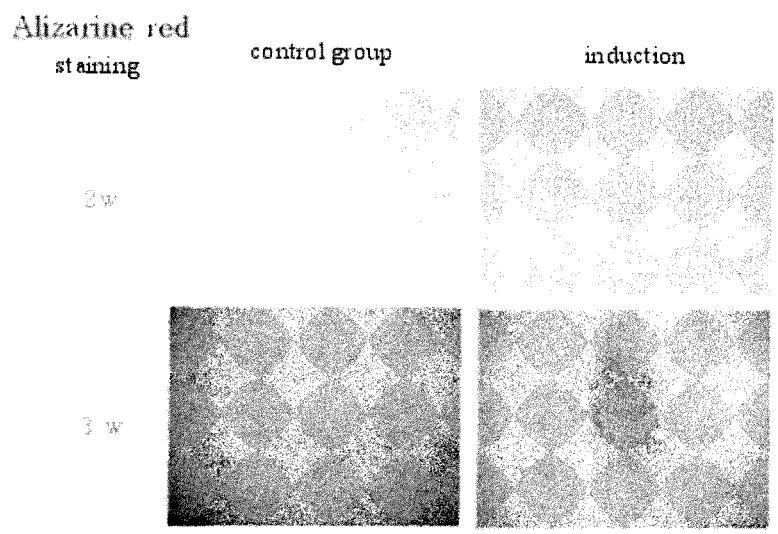
FIG. 14 is a picture showing the results of Alizarine red staining as osteogenic differentiation marker.

Further, FIG. 14 show the result of mineral staining with Alizarin red staining. No expression was observed at 2 weeks of differentiation, but partial staining at 3 weeks to confirm maturation differentiation into osteoblasts.

Differentiation into Adipocytes

Figure 15:
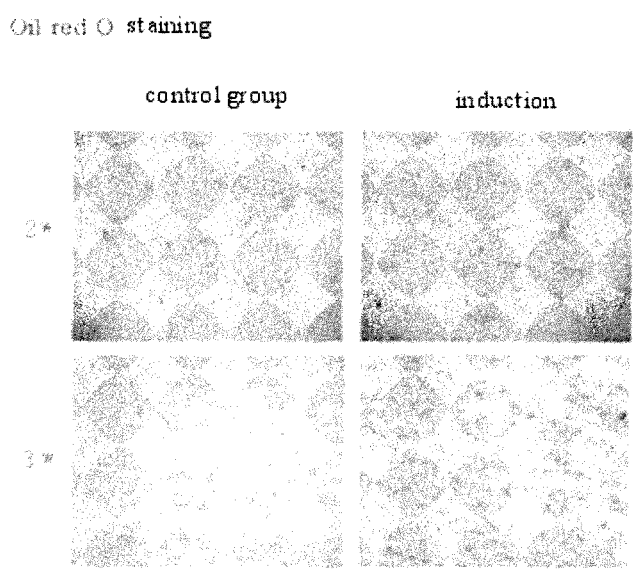
FIG. 15 shows the results of Oil red O staining for lipid droplets in the cells which are induced to be differentiated into adipocytes.

To confirm differentiation into adipocytes, the cells were stained with Oil Red 0 which particularly stains lipid droplets. As shown in FIG. 15, a number of lipid droplets stained with Oil Red 0 within the cells emerged to confirm differentiation into adipocytes.

Figure 16:
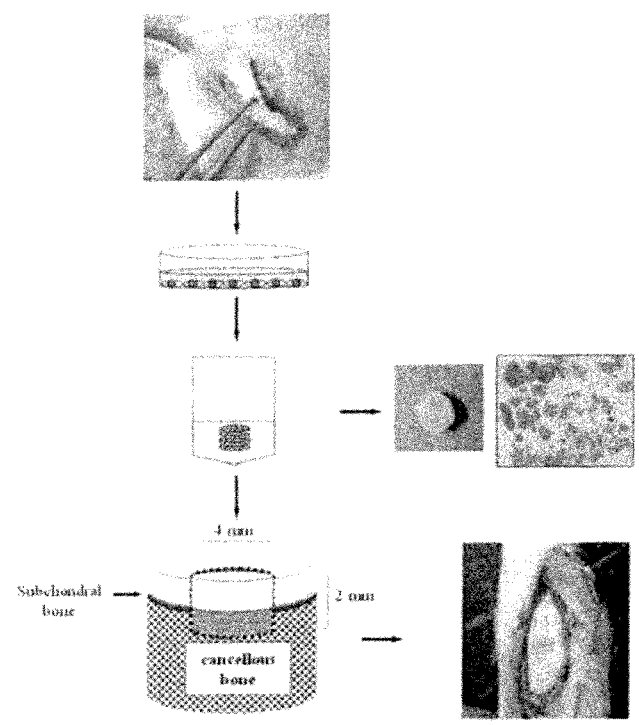
FIG. 16 is a schematic view showing the process for articular cartilage defect repair by costal chondrocytes loaded chitosan-based scaffolds.

Example 5: Evaluation of Repair Effect of Costal Chondrocytes within Chitosan-based Scaffold on Articular Cartilage Defects Materials and Methods The procedure of Example 5 is the same as the schematic view of FIG. 16. FIG. 16 shows the procedure where costal chondrocytes are isolated, cultured up to P2, and dedifferentiated cells are seeded onto chitosan-based scaffold, cultured, and the scaffold is transplanted into articular cartilage defect to repair cartilage defect.

Isolation of Chondrocytes

After taking the same procedure as the Example 1 above, the primary cells at confluence were subcultured up to P2.

Preparation of Sponge-form Scaffolds

COL-GAG Sponge:

The porous collagen matrix (Integra®, Integra Lifesciences Co., U.S.A.) was made of cross-linked bovine tendon collagen which is prepared to have a controlled porousness and predetermined degradation rate, and GAG (chondroitin-6-sulfate) fiber. The scaffold (COL-GAG) was made by 4 mm biopsy punch (S.F.M., Germany) and the silicon layer was removed by fine forceps.

CS Sponge:

Chitosan (Korea chitosan Co., Korea, 1.5% w/v) was dissolved in 0.1% aqueous acetic acid. After complete dissolution with sufficient agitation, this solution was passed 0.4 μm membrane filter (Millipore Co., U.S.A.) and was shared into molds. The casted gels were placed at −80° C. for 24 hours and then freeze-dried in a lyophilizer for 24 hours. The scaffolds were washed residue acid with alcohol and distilled water, and added acetic anhydride to acetylation. The scaffolds were washed sub-produced-acid with alcohol and distilled water and were freeze-dried. Thickness of chitosan scaffold (CS) was approximately 2 mm. Fine structure and pore size of chitosan scaffold were obtained by the scanning electron microscopy (SEM; FIG. 8). The scaffold having 4 mm diameter was made by 4 mm biopsy punch. Prior to the cell culture experiments, the scaffolds (CS) were sterilized by exposure to ultraviolet light for 30 minutes and were soaked with culture medium for 10 minutes. The prepared scaffolds were immediately used.

CS-HA Sponge:

After making 4 mm in diameter of chitosan scaffolds, they were soaked with 50% ethanol and were re-soaked with 0.1% hyaluronic acid (HA; Sigma, St Louis, Mo., U.S.A.) in PBS. The scaffolds were placed at −80° C. for 24hours and then freeze-dried in a lyophilizer for 24 hours. Prior to the cell culture experiments, the scaffolds (CS-HA) were sterilized by exposure to ultraviolet light for 30 minutes and were soaked with culture medium for 10 minutes. The prepared scaffolds were immediately used.

Chondrocytes Seeding onto Scaffolds and Culturing

COL-GAG, CS and CS-HA (4 mm in diameter×2 mm in thickness) were seeded with 2×10⁶ costal chondrocytes of second passage in medium volume of 20 μl, which had been placed in 6-well plates at 37° C. with 5% $CO_2$ for 2 hours. Subsequently, 6 ml of culture medium were added to each well and the cells were cultured for 4 weeks. The medium was changed every week and fresh L-ascorbic acid was added to the medium throughout the culture period every 72 hours. The culture soup and cell-scaffold constructs were obtained at 2, 7, 14 and 28 days, and the constructs only were obtained at 2 days.

MTT Assay, Blyscan Assay, Histological and Immunohistochemical Staining of the Cell-scaffold Constructs, and Procollagen Type I C-peptide (PIP) ELISA Assay MTT Assay The cell proliferation rates within each scaffolds were determined based on MTT assay (Mosman T. Rapid colormetric assay for cellular growth and survival, application to proliferation and cytotoxicity assays, J. Immunol. Methods 1983; 65: 55-63).

Procollagen Type I C-peptide (PIP) ELISA Assay

For quantitative determination of pro-C-peptide release from newly synthesized collagen, pro-collagen type I C-peptide (PIP) EIA Kit (Takara Bio. Inc., Japan) was used. The culture medium was diluted to 1:100 with distilled water and the rest of procedure was followed according to the manufacturer's specification. The absorbance was measured at 450 nm with a microplate reader (Bio Rad Lab., Richimond, Calif., U.S.A.). The amount of released peptide was calibrated with the standard curve in the range of 0-640 ng PIP/ml.

Blyscan Assay

The GAG content was determined quantitatively using a 1,9-dimethyl methylene blue assay (Blyscan® Glycosaminoglycan Assay, Biocolor, U.K.). Aliquot 300 μl of the culture medium was analyzed according to the manufacturer's specification and calibrated with standard curve measured by 0.1, 0.2, 0.3, 0.5, 1 and 2, μg of shark chondroitin sulfate (Sigma Chemical Co. St Louis, U.S.A.).

Statistics

Statistical analysis was carried out by the unpaired t test to determine whether variables were significantly different ($p<0.05$) in each experiment.

Animal Care

24 New Zealand white rabbits (initial weight 2.2 to 2.5 kg, about 4 to 5 months old) were used. Animals were regarded as young adults since perpendicular skeletal growth does not generally happen after 4 months old (Masoud et al., 1986). Animals were obtained 1 to 2 weeks before the experiments, and maintained under fixed light and darkness period (7:00 AM-7:00 PM, light period) and at fixed temperature of 22±2° C. and moisture of 50±7%. Animals were freely provided with water and food (standard lab digest (pellet type, Purina Co., Korea)), and were allowed to move freely in the ground. Animals were housed, supervised, and handled according to the approved national guidelines for animal care.

Surgical Procedure

Rabbits were anesthetized as described in the Example 1 above. Additional anesthesia was intravenous injection of a mixture of xyalzine and ketamine. Prior to operation, animals were intramuscularly administered with antibiotics (cefazoline, Jonggun-dang, Seoul, Korea) once.

The skin in the region of the knee was shaved, washed with alcohol, and prepared with povidone-iodine solution. The surgical approach was similar to that described by Shapiro et al. After a medial parapatellar incision was made, the patella was dislocated laterally to expose the patella groove of the femur. A defect 4 mm in diameter was created in the weight-bearing area of the patello-femoral joint by using a low-speed drill. This area is intermittently weight-bearing in the rabbit and contacts the patella bone. The conical full-thickness defects extended from the surface of the articular cartilage through the compact subchondral bone into the cancellous bone in the marrow space of distal femur. The depth of the defects was approximately 2.0 to 2.5 mm. After drilling, the defect was irrigated extensively with cold saline (NaCl 0.9% w/v) to remove loose fragments. A drop of a fibrin adhesive system (Tisseel® Kit, Baxter AG, Austria) was applied into the defects to fix the transplanted construct in the defect and immediately scaffold was inserted into the defects. In the control defects, only fibrin sealant was used (FIG. 16). The dislocation of patella was reduced and the joint capsule and skin were sutured in layers. Any cast was not applied and the rabbits were allowed to move freely in their field immediately after recovery from anesthesia. Intramuscular injections of cefazoline were performed twice a day for 5 days. Knees of animals were separated into three groups: (1) untreated defects (Control); (2) treated with CS-HA alone (S); or (3) treated with costal chondrocytes-laden CS-HA (S-CELL). At 6 and 12 weeks from the implant, rabbits were euthanized with an injection of $MgSO_4$ under deep anesthesia.

Histological Evaluation for Repair Tissues

After the sacrifice of the animals, their knees were examined for the gross morphology (color, integrity, contour and smoothness), repair of the defects and appearance of the surrounding cartilage. The specimens of the implantation areas were dissected, photographed and fixated with 10% buffered formalin for a week at room temperature. Samples were then rinsed to eliminate the excess fixative and decalcified by Calci-Clear Rapid (National Diagnotics, U.S.A.) for a week. They were dehydrated by grading ethanol and xylene and embedded in paraffin. 6 μm thick sections were cut by a microtome for histological studies. Sections were stained with hematoxylin and eosin (H & E) for the study of morphologic detail and with Safranin-O and fast green to assess GAG distribution.

Evaluation of Cartilage Defects

The sections were evaluated blindly by two investigators using a modified histological grading scale from those of Pineda et al (1992) and Wakitani et al (1994). The grading scale was totally composed of 5 categories with a total range of points from 0 (normal cartilage) to 14 (no repair tissue) (Table 4).

TABLE 4

Histological grading scale for the defects of cartilage

| Category | Points |
| --- | --- |
| Cell morphology | |
| Hyaline cartilage | 0 |
| Mostly hyaline cartilage | 1 |
| Mostly fibrocartilage | 2 |
| Mostly non-cartilage | 3 |
| Non-cartilage only | 4 |
| Matrix staining (metachromasia) | |
| Normal (compared with host adjacent cartilage) | 0 |
| Slightly reduced | 1 |
| Significantly reduced | 2 |
| No metachromatic stain | 3 |
| Surface regularity | |
| Smooth ($>3/4^a$) | 0 |
| Moderate ($1/2 < 3/4^a$) | 1 |
| Irregular ($1/4 < 1/2^a$) | 2 |
| Severely irregular ($<1/4^a$) | 3 |
| Thickness of the cartilage | |
| $0 > 2/3^b$ | 0 |
| $1/3 > 2/3^b$ | 1 |
| $<1/3^b$ | 2 |
| Integration of donor with host adjacent cartilage | |
| Both edges integrated | 0 |
| One edge integrated | 1 |

TABLE 4-continued

Histological grading scale for the defects of cartilage

| Category | Points |
| --- | --- |
| Neither edge integrated | 2 |
| Total maximum | 14 |

[a]Total smooth area of reparative cartilage compared with the whole area of the cartilage defect.
[b]Average thickness of reparative cartilage compared with that of surrounding cartilage.

Statistical Analysis

Statistical significance was evaluated by using t-test. The significance level was $p<0.05$.

Results

Costal Chondrocytes Cultured in Sponge-form Scaffolds

Figure 17:
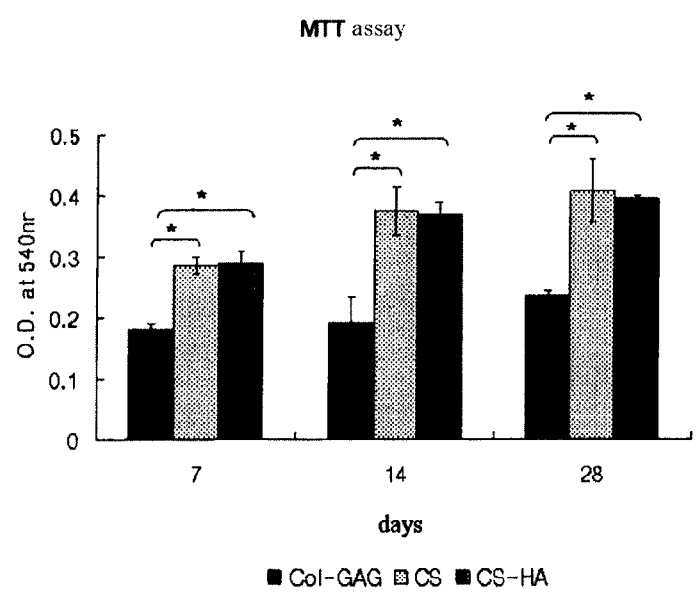
FIG. 17 is a graph showing comparison of chondrocytes growth rate in Col-GAG, CS and CS-HA by MIT assay.

The proliferation rates of costal chondrocytes in three different scaffolds; collagen-GAG sponge (COL-GAG), chitosan sponge (CS), and HA-coated chitosan sponge (CS-HA), were compared at 1, 2 and 4 weeks of culture using MTT assay (FIG. 17).

The value in FIG. 17 shows cell proliferation inside these scaffolds. The O.D. value of the CS and CS-HA were gradually increased with the culture time and there was no notable difference between two scaffolds. Similar trend was found in COL-GAG, but initially started low level. At 28 day culture, the O.D. values compared with that at 7 day culture, were increased approximately 1.30, 1.43 and 1.40 folds in COL-GAG, CS and CS-HA, respectively.

Figure 18:
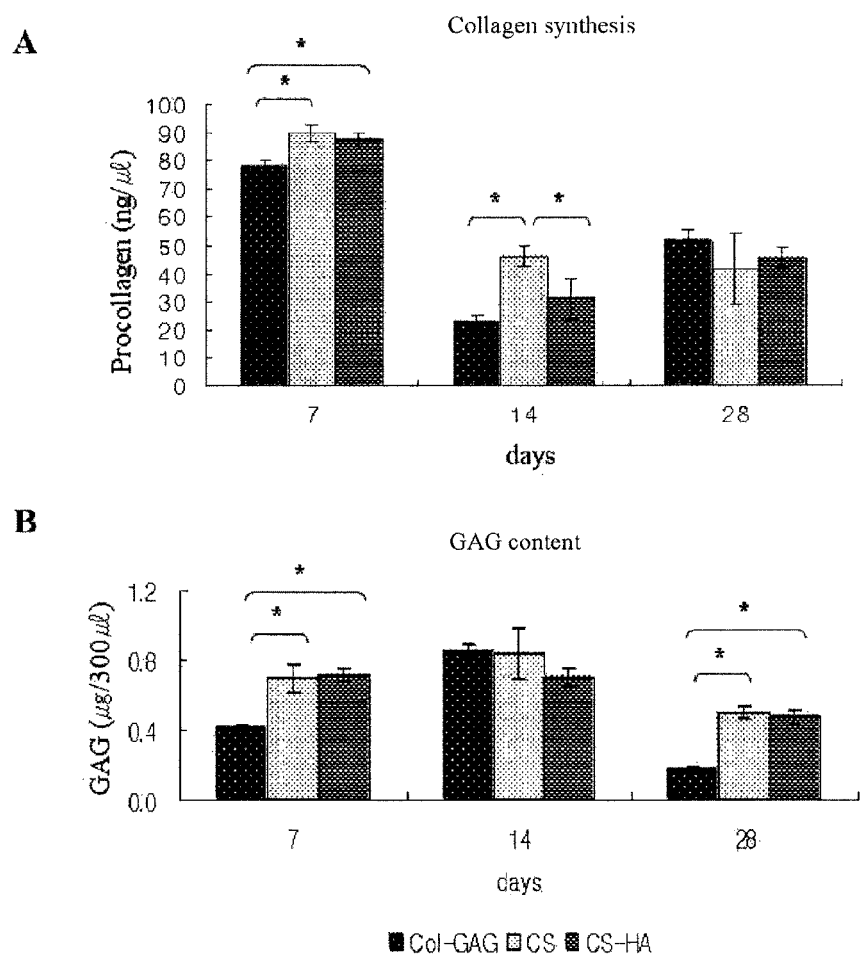
FIG. 18 shows the results of the amount of PIP and GAG measured.

To estimate neosynthesis of collagen of the cell seeded composite scaffolds, procollagen Type I C-peptide (PIP) was measured by ELISA assay (FIG. 18). At 7 day culture, collagen syntheses of CS and CS-HA were more than that of COL-GAG with significant difference. However, at 14 days, collagen synthesis in CS was more extensive than in COL-GAG and CS-HA (CS>CS-HA>COL-GAG). Compared with at 7 day culture, collagen synthesis at 14 day culture was significantly decreased. During four-week culture period, in CS, collagen secretion to culture medium was gradually decreased, on the contrary, in COL-GAG and CS-HA, collagen release were significantly decreased between 1 and 2 weeks, and then increased between 2 and 4 weeks.

Blyscan assay revealed that the amounts of GAGs released from the costal chondrocytes-seeded three different scaffolds into culture supernatant for a week (FIG. 18). At the 1 week of culture, both chitosan scaffolds released more GAGs than COL-GAG. At the 14 days, the released amounts of GAGs were similar in all three scaffolds, but at the 28 days of culture, the relseased GAG amounts in COL-GAG were very smaller than in CS and CS-HA.

During rabbit costal chondrocytes were seeded onto COL-GAG, CS and CS-HA and cultured for 28 days, CS and CS-HA were bigger in size than COL-GAG throughout the culture time.

Figure 19:
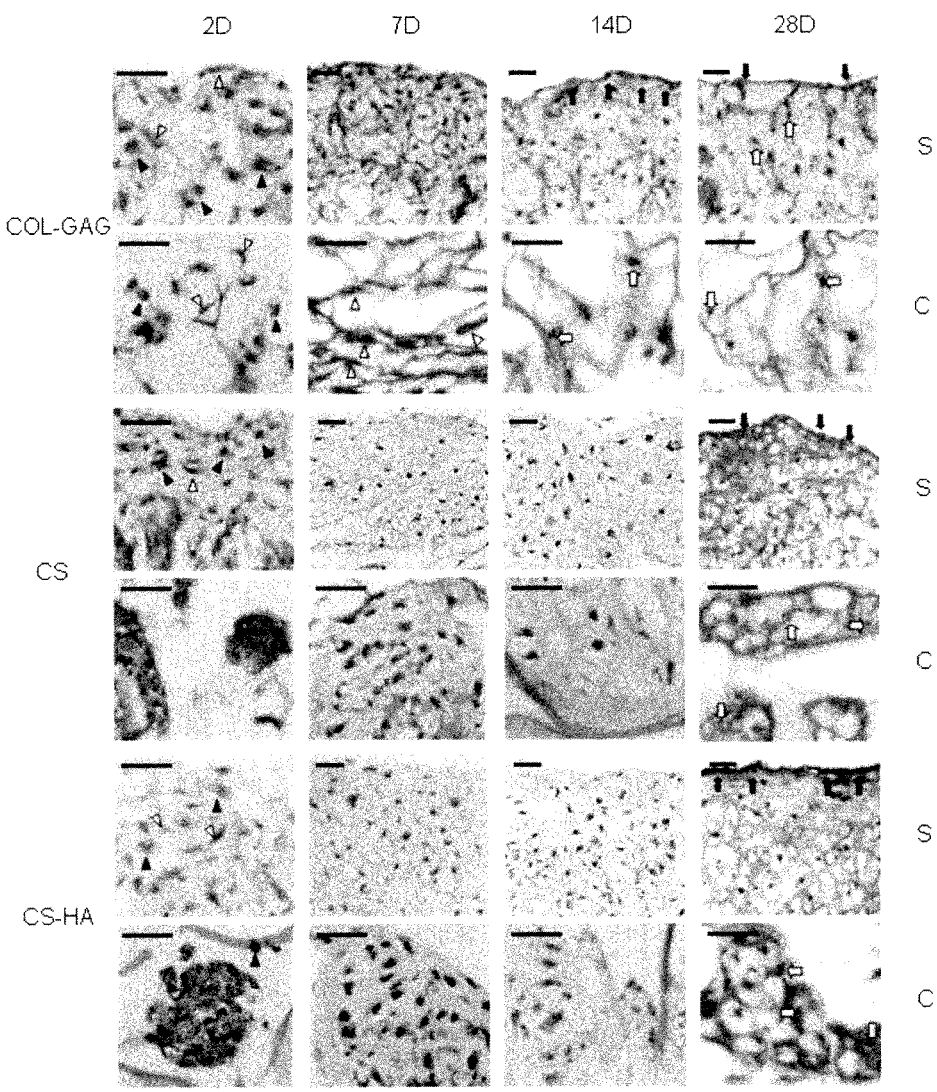
FIG. 19 shows cells morphology by H & E staining.

Histological examination of these specimens using H & E stains revealed morphologic characteristics (FIG. 19). In FIG. 19, S represents surface, C represents center, scale bar represents 50 µm, black arrow represents fibrous tissue, white arrow represents death cell, black arrow head represents round-shaped cell, and white arrow head represents spindle-shaped cell. After 2 day chondrocytes culture, the seeded cells were mainly presented in the superficial area of both chitosan-based scaffolds and especially COL-GAG. Round and spindle-shaped cells were mixed and no cell was occupied in lacunae at 2 days. The cells in the center of the CS and CS-HA were aggregated but in the COL-GAG, the cells in the center were rare and dispersed at 2-day specimen.

After 7 days of culturing, the increase of the cell number was notable in the periphery of the scaffolds, and new cell peripheral matrices surrounded most of the cells. In the center and the periphery of both CS and CS-HA scaffolds, the vast majority of the seeded cells had maintained their spherical morphology, occupied in lacunae, and synthesized abundant matrices. However, in COL-GAG, the cells of the periphery were round morphology, but they were not occupied in lacunae, and the cells in the center were spindle-shape morphology and were not aggregated.

At 14 day of culture, the vast majority of the cells in the center and the periphery of both chitosan-based scaffolds had still maintained their spherical morphology, occupied in lacunae, and synthesized much abundant extracellular matrices. But in COL-GAG, cells of the periphery were spherical morphology, occupied in lacunae, and synthesized abundant extracellular matrices, but cells of the center were still spindle-shaped, had small lacunae, and synthesized a little ECM.

At the end of the experiment (28 days), the surface of both chitosan-based scaffolds was covered with thin fibrous tissue. The cells in the center as well as in the periphery became small, were still occupied in large lacunae. In COL-GAG, the cells in the periphery decreased cellularity, had very small round morpholohgy, and did not have lacunae. The cells in the center were similarly at 14 days.

Figure 20:
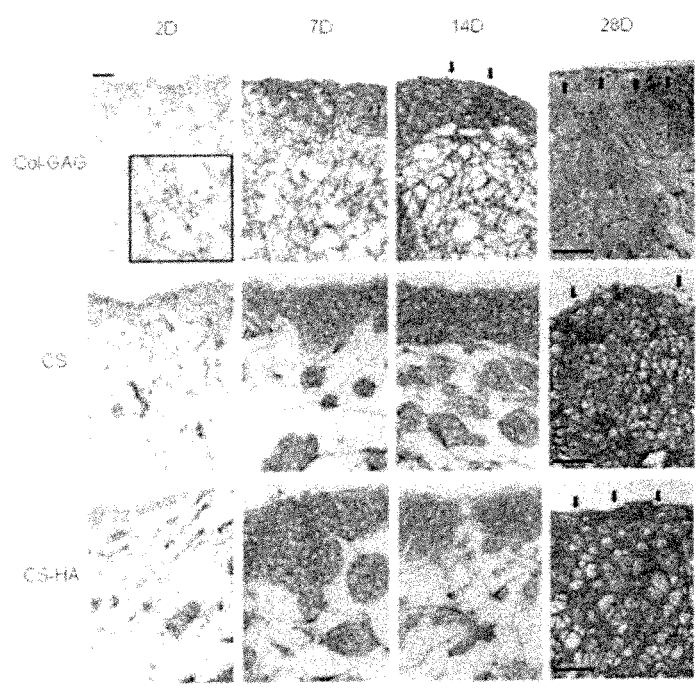
FIG. 20 shows GAG accumulation by Safranin-O staining and fast green staining.

Histological staining for cartilaginous ECM of GAG by Safranin-O fast green (S/O) staining revealed that GAG was detected in the CS and CS-HA scaffolds in the center of the scaffolds throughout the period of culture (FIG. 20). In FIG. 20, white arrow head represents Safranin-O stained frame, black arrow represents fibrous tissue, white arrow represents fast green stained cells, and scale bar represents 100 µm. In both chitosan-based scaffolds, cells in the center were stained with S/O from 2 day culture specimens. However, in COL-GAG, cells in the center were not stained with S/O. The amount of accumulated GAG increased with an increase of the culture time in the three types of scaffolds. At 28 day culture, the surrounds of the scaffolds were not stained with fast green.

No GAG was histological detected in the CS and CS-HA without chondrocytes, but the frame of COL-GAG was positively stained with S/O because they conjugated with chondroitin sulfate.

Immunostaining for Type I and Type II Collagen

In both chitosan-based scaffolds, type I collagen was not detected in 1 and 2 week specimens. On the contrary, anti-type II collagen antibody was strongly positive in both chitosan-based scaffolds during 1 to 2 weeks culture period. At 4 weeks, some portions of cell aggregates in the surface and center of the scaffolds were positive with anti-type I collagen antibody. However, in the 4 week specimen, anti-type II collagen antibody was still positive, but became weak.

Figure 21:
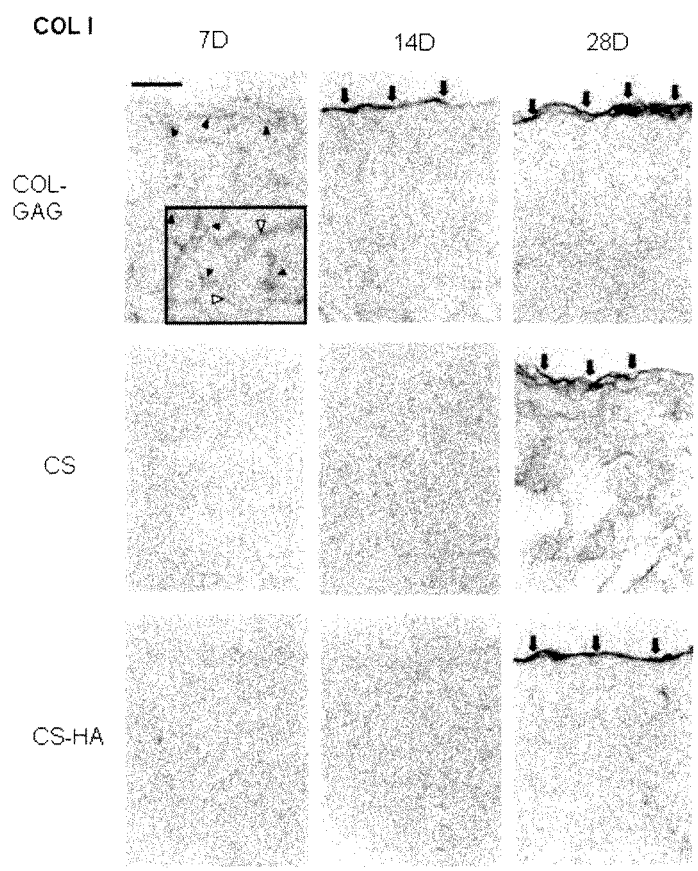
FIGS. 21 and 22 show the results of immuno-staining for type I collagen and type II collagen, respectively.
Figure 22:
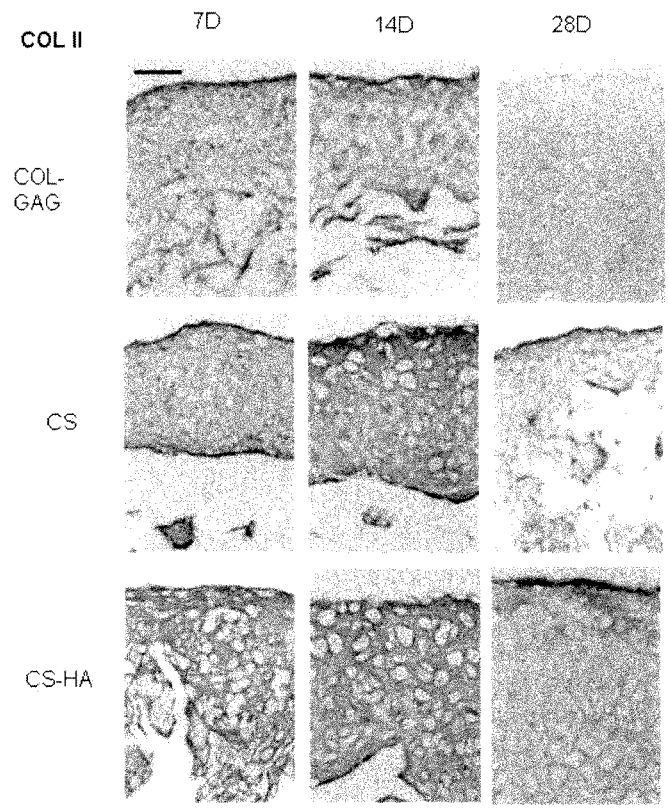

In COL-GAG, type I collagen was detected in all 1, 2 and 4 week specimens. Anti-type II collagen antibody was positive in only the surface at 1 week, and in the matrices of the periphery and a few of cells in the center at 2 weeks. In the 4 week specimen, anti-type II collagen antibody was very weakly positive (FIGS. 21 and 22). In FIG. 21, black arrow represents fibrous tissue, black arrow head represents type I collagen expressing cell, white arrow represents COL-GAG frame, and scale bar in FIGS. 21 and 22 represents 100 µm.

As a result of the histological observation above, when dedifferentiated chondrocytes were seeded onto three types of sponge form scaffolds (CS, CS-HA and COL-GAG), in both chitosan-based scaffolds, the seeded cells were redifferentiated in morphology, GAG synthesis and type II collagen expression for 1 to 2 weeks. However, in COL-GAG, internal cell seeding was not effective, and redifferentiation of cells in the center was not good. Very lately, at 4 weeks, cells began to lose synthesized ECM activity (the size of lacunae became smaller).

In vivo Results

This study was designed to evaluate the role of cultured costal chondrocytes-chitosan composite in the repair of full-thickness articular cartilage defects in a weight-bearing animal model.

Costal chondrocytes at P2 were seeded onto CS-HA scaffolds, and cultured for 2 weeks. Cartilage defects were surgically made on rabbit patella groove of the femur. Animals were euthanized, and the knee joints were obtained at 6 and 12 weeks. The specimens were analyzed macroscopically, histologically and immunohistochemically.

Clinical Test

No postoperative complications occurred in any of the experimental animals. During the study, no symptom of articular outflow and disability was observed.

Gross Appearance

Upon gross observation, no symptom of synovial membrane outflow or synovitis was observed in any joint. Although synovial tissue histology was not performed, there was no gross evidence of an inflammatory reaction. Grossly, the synovial fluid in all joints was normal in terms of quantity, viscosity, and color.

In FIG. 23 to FIG. 26, Control represents the control group, S represents CS-HA grafted defect, and S-CELL represents costal chondrocytes-seeded CS-HA grafted defect.

Empty (Control) Defect

Figure 23:
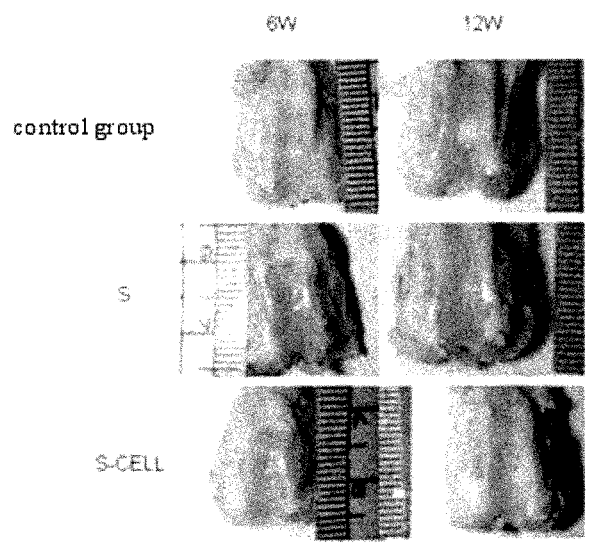
FIG. 23 is a picture showing gross appearance of repair tissue of articular cartilage defect.

At 6 weeks after transplantation, in the control group, the defects were seen smooth surface. The defects had a gap or lack of continuity between the repair tissue and the adjacent articular cartilage. The margins of the defects were discernable. The repair tissue was whiter and slightly opaque compared with the adjacent normal cartilage (FIG. 23). At 12 weeks after transplantation, the repair tissues in the control group were easily distinguished from the normal adjacent cartilage because they had white and opaque appearance. The defects were completely filled with smooth white repair tissue (FIG. 23).

CS-HA Grafted Defect

Grossly at 6 weeks, some of the defects were not completely filled with repair tissue, and in some areas subchondral bone was exposed. The surface of the repair tissue in the defects was more irregular than that surrounding normal, and the margins of the repair tissue were not smooth. The repair tissues were white to pink appearance and translucence (FIG. 23). At 12 weeks, the repair tissues of CS-HA grafted defects were still discernible, but were hyaline in appearance and texture. And, the defects were filled to the level of the adjacent normal cartilage. The surface of some of them was smoother than that of 6-week specimen. In some cases (1/8), the repair tissues were filled with not cartilage, but bone (FIG. 23).

Costal Chondrocytes-laden CS-HA Grafted Defect

At 6 weeks, all the defects were filled with repair tissues, and the margins of the defects were discernable from the adjacent normal cartilage. The surface and the edges of the repair tissue were rough and irregular. The repair tissue was hyaline in appearance and texture (FIG. 23). Grossly at 12 weeks, all the repair tissues formed the level of the surrounding normal cartilage. The surface and the edges of the repair tissue were smoother than that of 6-week specimen. The repair tissue could still be distinguished from the surrounding normal cartilage. But the edges of the repair cartilage were more smooth integrated with the normal cartilage than that in 6-week specimen (FIG. 23).

At 6 weeks, gross appearance of CS grafted defects was similar to that of cells-laden CS grafted defects: both of them were white and somehow irregular. Up to 12 weeks, in general, the surface of the control defects was much smoother than that of CS grafted defects wherein the surface is protruded and irregular. The surface of the control defects was white appearance, but that of grafted defects was pink appearance. The color and texture of the repair tissue in cell-laden grafted defects were similar to those of the adjacent normal cartilage.

Morphology

Control Defect

Figure 24:
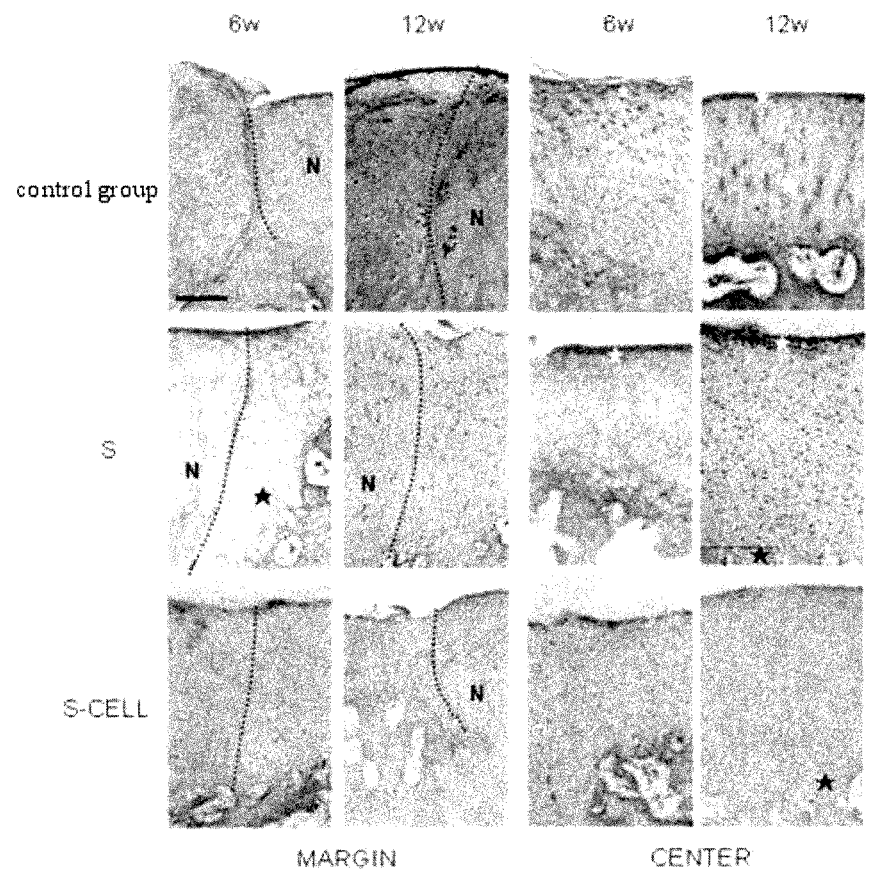
FIGS. 24 to 26 are pictures showing repair tissue of articular cartilage defect by optical microscope.
Figure 25:
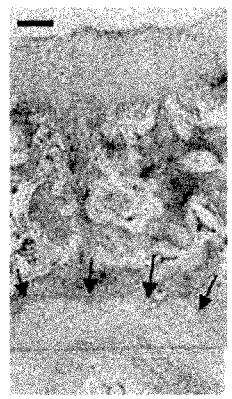
Figure 26:
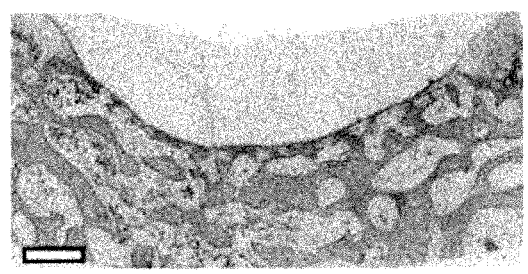

At 6 weeks after transplantation, addition resembling fibrocartilagious tissue formation was seen at the graft copula. The defects had a gap or lack of continuity between the repair tissue and the adjacent articular cartilage on one or both sides. This observation indicates decrease in integration between the surrounding articular artilage and the repair tissue. The interface between the repair cartilage and the adjacent normal cartilage occasionally showed fibrillar continuity. The surface of the repair tissue was composed with 3 to 5 layer of flattened cell and was fibrillation. The repair tissue consisted of a mixture of fibrous tissue and hypercellular fibrocartilage. Some defects showed cracked gap in fiber and fibrocartilagious reparative cartilage. The repair tissue recovered subchondral bone in good degree (FIGS. 24 to 26).

At 12 weeks, some of the cartilage defects had a gap or lack of continuity between the repair tissue and the adjacent normal cartilage. The surface of the repair tissue was smooth and well fibrillation. The defects were filled with chondrocytes and matrices. However, fibroblasts are predominant in the surface layer, and most of the surface were consisted of fibrous matrices. The repair tissues had a fine ECM resembling fibrous cartilage and were involved with round, relatively mature chondrocyte-like cell. So the repair tissues of the control group at 12 weeks were consisted predominantly of fibrous tissue and fibrocartilagious tissue (FIGS. 24 to 26).

CS-HA Scaffold Grafted Defect

At 6 weeks, the repair tissues were good integration with the adjacent normal cartilage. In microscopic view, the repair tissues were hypercellular components. The repair tissues were predominantly hypertrophic chondrocytes, and flattened superficial cells in osteochondral defects treated with chitosan-based sponge. The bottom of the repair tissue was composed spindle-shaped cells which have irregular ECM and are similar to immature substantial cell. The repair tissue was hyaline and fibrous cartilage. A few cell layers on the surface of the defects were small and flattened, and ECM was stained with H & E. Almost all the fibrous tissues were found at the surface of the repair tissue. The middle layer of the repair tissue had hyaline cartilage like tissue, which involved with round and large nucleus, relatively immature chondrocyte-like cell (FIGS. 24 to 26). However, the repair cartilage was seen perpendicular crack, but not very often.

At 12 weeks, the repair tissue and the adjacent normal cartilage were integrated well. After 12 weeks of transplantation, the repair tissue had predominantly immature chondrocytes and flattened superficial cells in osteochondral defects treated with chitosan-based sponge. The elongated fibroblasts were aligned parallel to the surface and the defect was filled with high density immature chondrocytes and hyaline-like matrices. The bottom of the repair cartilage involved hypertrophic chondrocytes and well restored to subchondral bone. Occasionally, some of the defects were filled with not cartilaginous tissue but osseous tissue that covered with thin fibrous tissue (FIGS. 24 to 26).

Costal Chondrocytes-laden CS-HA Scaffold Grafted Defect

In the 6 week specimens, chondrocytes in the reparative tissue were greater numbers than in adjacent normal cartilage, and they were columnar organized. Some part of the surface was evidence of fibrillation. The repair cartilage showed a normally integration with the surrounding normal cartilage and the bony portion. Any defects showed cracked gap in the repair cartilage (FIGS. 24 to 26). Bone trabecules developed in the deep zone of the graft, enclosing small residue chondrocyte-island was seen in the cancellous bone.

At 12 weeks, the defects treated with the cultured cell-laden CS-HA were completely filled with cells and matrix. The repair tissue was normally integration with subchondral bone and adjacent normal cartilage. Any defects showed cracked gap in the repair cartilage. The reparative tissue involved with single or multiple chondrocytes within single lacunae and they consisted isogenous groups and were columnar arranged. The repair tissue had abundant extracellular matrix and orderly aligned chondrocytes, and no detect had fibrillation of the surface although slight rough surface was seen. The chondrocytes of 2 to 4 layers in the surface were small and flattened-shape, and involved lacunae. The chondrocytes in the bottom of the repair tissue were large and round cells and hypertrophied, larger number than them in the surface. The repair cartilage was predominantly hyaline cartilage. The thickness of the hyaline cartilage formed in these defects was thinner than that of the adjacent normal cartilage (FIGS. 24 to 26).

GAG Distribution—Safranin-O Staining

Control Defect

Figure 27:
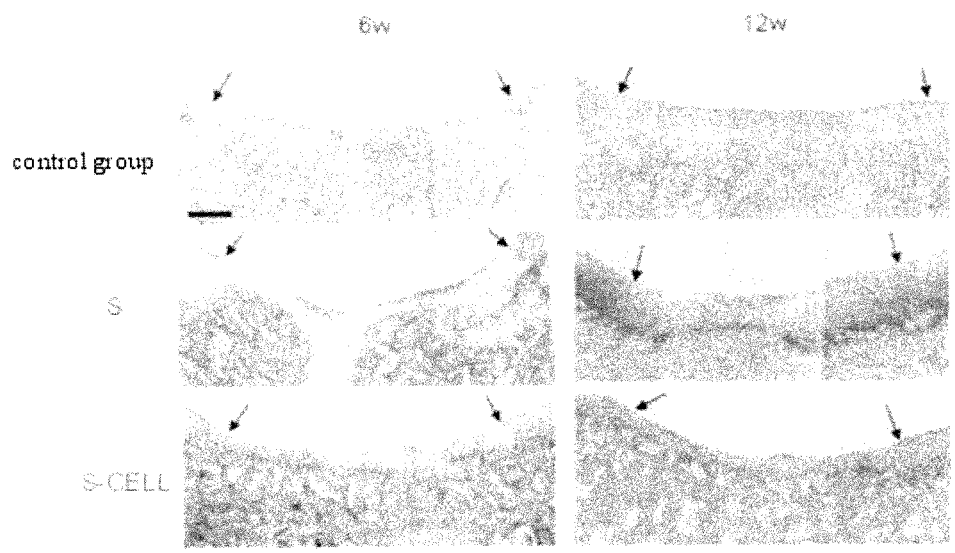
FIG. 27 shows the results of Safranin-O staining for GAG distribution in repair tissue of articular cartilage defect.

At 6 weeks, in the control defects, only some area in the bottom of the repair tissue was stained with S/O. The other repair tissue was not stained with S/O, and the surface of the repair tissue was stained with fast green, opposite staining color. A moderate to severe loss of metachromasia was apparent in the control defect sections (FIG. 27). At 12 weeks, the surface of the repair tissue was still stained with fast green. Only in one case, the repair tissue was stained with S/O, and the other cases were negative stain for S/O (FIG. 27).

CS-HA Scaffold Grafted Defect

At 6 weeks, the areas filled with hypertrophied chondrocytes were positive stain with S/O, and the adjacencies to the surrounding normal cartilage were weakly stained. Safranin-O and fast green staining was evident predominantly in the area of hypertrophic chondrocytes at the bottom of the defects (FIG. 27). At 12 weeks, the bottom of the reparative tissue and the adjacencies to the surrounding normal cartilage were more strongly stained with S/O than that at 6 weeks (FIG. 27).

Costal Chondrocytes-laden CS-HA Scaffold Grafted Defect

At 6 weeks, all of the repair tissue were stained with S/O but slightly or moderately decreased as compared to the surrounding normal cartilage, and the bottom of the repair tissue was strongly positive for S/O. The staining intensity of the repair cartilage decreased weakly or moderately as compared to the adjacent normal cartilage (FIG. 27). At 12 weeks, the repair tissue was stained with S/O to the level of the surrounding normal cartilage except some areas in the center. Most of the repair cartilage was seen hyaline-like, and the defect showed perpendicular columnar chondrocytes in the radius area.

Immunostaining for Type I and Type II Collagen

Control Defect

Figure 28:
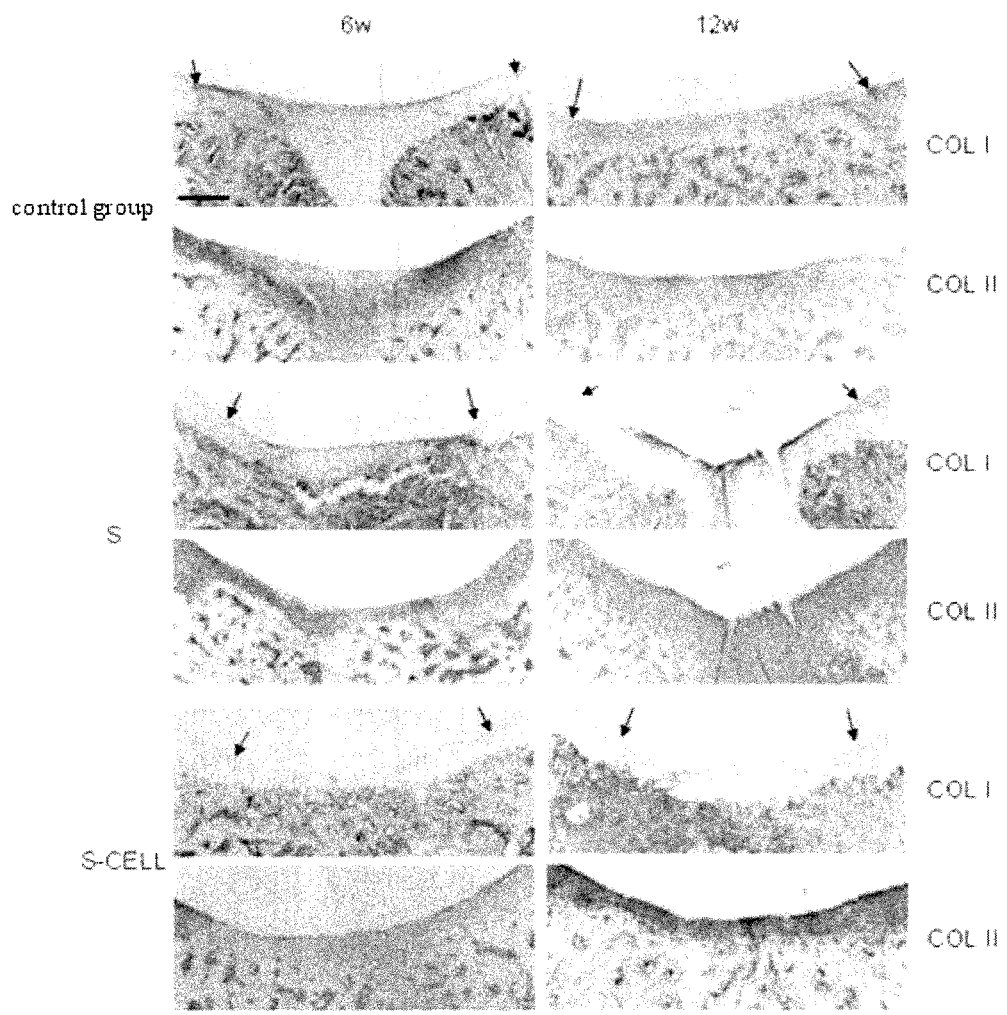
FIG. 28 shows the results of immuno-staining for type I and II collagen in repair tissue of articular carilage defect.

At 6 weeks after transplantation, half of the upper portion of the repair tissue and the adjacencies to the normal cartilage were positive with anti-type I collagen. The other portions except the calcified cartilage were positive with anti-type II collagen (FIG. 28). At 12 weeks, the cells in whole portions of the repair tissue were positive with anti-type I collagen (FIG. 28).

CS-HA Grafted Defect

At 6 weeks, the edges and upper portion of the repair tissue were positive with anti-type I collagen. The hypertrophied portion was also positive with anti-type I collagen (FIG. 28). At 12 weeks, the surface of the repair tissue was positive with anti-type I collagen, and the others were anti-type II collagen (FIG. 28).

Costal Chondrocytes-laden CS-HA Scaffold Grafted Defect

At 6 weeks, some portions of the surface of the repair tissue were positive with anti-type I collagen. Anti-type II collagen expression was reduced in the repair tissue compared to the adjacent normal cartilage (FIG. 28). At 12 weeks, in the small portion of the surface, anti-type I collagen was slightly positive expression. The repair tissue expressed anti-type II collagen in a similar level to the normal cartilage (FIG. 28).

The results of the histological grading scale (mean score) was shown in Table 5.

TABLE 5

Results of the histological grading scale

| | Control | | S | | S-CELL | |
|---|---|---|---|---|---|---|
| | 6 w | 12 w | 6 w | 12 w | 6 w | 12 w |
| Cell morphology | 1.67 ± 0.58[a] | 2.5 ± 0.84 | 2.25 ± 0.96 | 2.5 ± 1.2 | 1.75 ± 0.96 | 1 ± 0.71 |
| Matrix stain | 2 ± 0 | 2.5 ± 0.84 | 2.5 ± 0.58 | 2.13 ± 0.83 | 2 ± 0.82 | 0.8 ± 0.45 |
| Surface regularity | 0.33 ± 0.58 | 1.17 ± 0.75 | 0.5 ± 1 | 1 ± 0.76 | 0.75 ± 0.5 | 0.4 ± 0.55 |
| Thickness of cartilage | 0 ± 0 | 0.5 ± 0.84 | 1.25 ± 0.96 | 1.25 ± 0.89 | 0.75 ± 0.96 | 0.8 ± 0.45 |
| Integration with host adjacent cartilage | 1 ± 0 | 0.67 ± 0.52 | 0 ± 0 | 0.13 ± 0.35 | 0 ± 0 | 0.2 ± 0.45 |
| Total | 5 ± 1 | 7.33 ± 2.4 | 6.5 ± 3.11 | 7 ± 2.62 | 5.25 ± 2.99 | 3.2 ± 1.79 |

[a]represented by S.D.

Example 6: Evaluation of Repair Effect of MSC-like Dedifferentiated Cells within Chitosan-based Scaffold on Articular Cartilage Defects Materials and Methods Isolation and Culture of Chondrocytes As the Example 1, costal chondrocytes were isolated from costa by enzyme treatment, plated at a cell density of $5\times10^5$ cells/100 mm diameter Petri dish, and subcultured in MSCGM added with 1 ng/ml of FGF up to P8 as the Example 3, to obtain MSC-like dedifferentiated cells.

Preparation of MSC-like Dedifferentiated Cells within Chitosan-based Scaffolds and Culture As the Example 5, chitosan sponge was prepared and coated with HA. The CS-HA sponges in 5 mm diameter were seeded with 2×106 MSC-like dedifferentiated cells at P8 to obtain MSC-like dedifferentiated cells within scaffolds, and cultured in chondrogenic medium containing TGF-beta for 2 weeks to induce into cartilage differentiation. For the estimation of the degree of differentiation into cartilage, Safranin-O staning was performed.

Repair Effect on Articular Cartilage Defect

As the Example 1, the rabbits were anesthetized, and administered antibiotics prior to operation. Defects (5 mm diameter, approximately 2.0 to 2.5 mm depth) were made on the patellar grooves of the both femur, and grafted with MSC-like dedifferentiated cells (already differentiated into cartilage) within scaffold as the Example 2.

Results

Redifferentiation into Chondrocytes

Figure 29:
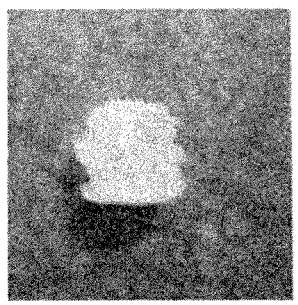
FIG. 29 is a macroscopic picture of the artificial cartilage from MSC-like dedifferentiated cells loaded chitosan-based scaffolds in chondrogenic medium.

FIG. 29 is a macroscopic picture of the artificial cartilage containing redifferentiated chondrocytes obtained by loading MSC-like dedifferentiated cells from costal chondrocytes onto chitosan sponge and redifferentiating them in chondrogenic medium.

Figure 30:
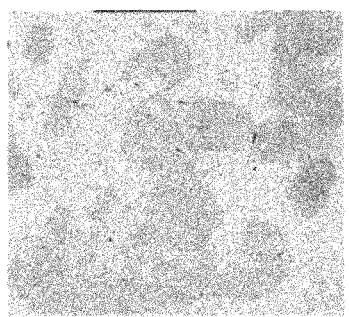
FIG. 30 shows the results of Safranin-O staining for GAG in chondrocytes redifferentiated in chondrogenic imdium.

FIG. 30 shows the results of Safranin-O staining for GAG in chondrocytes redifferentiated in chondrogenic imdium. After 2 weeks of chondrogenic differentiation, MSC-like dedifferentiated cells in the sponge were redifferentiated into chondrocytes.

Articular Cartilage Defect Repair

Figure 31:
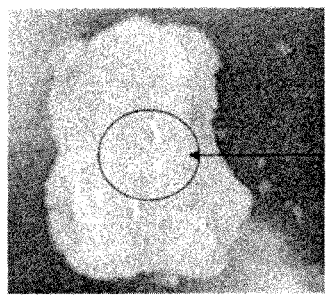
FIG. 31 is a macroscopic picture of rabbit articular cartilage defect at 6 weeks after transplantation with MSC-like dedifferentiated cells loaded chitosan-based scaffolds.

FIG. 31 is a macroscopic picture of rabbit articular cartilage defect at 6 weeks after transplantation with MSC-like dedifferentiated cells laden chitosan-based scaffolds. The repair tissue was smoothly integrated with the adjacent normal tissue, and was seen hyaline cartilage in appearance and texture.

INDUSTRIAL APPLICABILITY

In the present invention, it was first disclosed that costal cartilage provides higher cell yield and cell expansion rate than articular cartilage, and so costal cartilage is better cell source for cartilage repair than articular cartilage. Before the present invention, it was known in the art that dedifferentiation rate, that is, loss of chondrocytic phenotype during the culture of chondrocytes was significantly high which limits ACT application. However, surprisingly, in the present invention, it was confirmed that dedifferentiated chondrocytes during the passage of costal chondrocytes obtained from costal cartilage show MSC properties, and so such fully dedifferentiated costal chondrocytes can be differentiated into desired differentiated cells such as osteoblasts, adipocytes, etc, as well as chondrocytes when recultured in differentiated condition. Thus, the present invention provides an artificial cartilage and cell therapeutic agent containing MSC-like dedifferentiated cells obtained by passaging costal chondrocytes.

In addition, the present invention showed that autologous costal chondrocytes-loaded chitosan-based scaffold when transplanted into cartilage defect can very effectively repair full-thickness articular cartilage defects in a weight-bearing site.

What is claimed is:

1. A process for preparing an artificial cartilage comprising:
    passaging costal chondrocytes in fibroblast growth factor (FGF)-containing mesenchymal stem cell growth medium (MSCGM) to obtain MSC-like dedifferentiated cells; and
    obtaining the artificial cartilage,
    wherein the dedifferentiated cells exhibit a fibroblastic spindle shape, MSC properties and an increased expression of cartilaginous extracellular matrix when redifferentiated into cartilage.

2. The process of claim 1, which further comprises culturing the MSC-like dedifferentiated cells in a chondrogenic medium to obtain redifferentiated chondrocytes.

3. The process of claim 2, which further comprises pellet culturing the MSC-like dedifferentiated cells in a chondrogenic medium to obtain redifferentiated chondrocytes.

4. The process of claim 1, which further comprises loading the MSC-like dedifferentiated cells on a chitosan-based scaffold.

5. The process of claim 1, which further comprises loading the MSC-like dedifferentiated cells on a chitosan based scaffold and passaging costal chondrocytes in fibroblast growth factor (FGF)-containing mesenchymal stem cell growth medium (MSCGM) from passage 4 to passage 8.

* * * * *